(12) United States Patent
Pulliam et al.

(10) Patent No.: US 9,782,122 B1
(45) Date of Patent: Oct. 10, 2017

(54) PAIN QUANTIFICATION AND MANAGEMENT SYSTEM AND DEVICE, AND METHOD OF USING

(71) Applicants: Christopher L Pulliam, Shaker Heights, OH (US); Joseph P Giuffrida, Hinckley, OH (US)

(72) Inventors: Christopher L Pulliam, Shaker Heights, OH (US); Joseph P Giuffrida, Hinckley, OH (US)

(73) Assignee: Great Lakes NeuroTechnologies Inc, Cleveland, OH (US)

( * ) Notice: Subject to any disclaimer, the term of this patent is extended or adjusted under 35 U.S.C. 154(b) by 254 days.

(21) Appl. No.: 14/613,678

(22) Filed: Feb. 4, 2015

Related U.S. Application Data

(60) Provisional application No. 62/015,717, filed on Jun. 23, 2014.

(51) Int. Cl.
*A61B 5/00* (2006.01)
*A61B 5/11* (2006.01)
(Continued)

(52) U.S. Cl.
CPC .............. *A61B 5/4824* (2013.01); *A61B 5/11* (2013.01); *A61B 5/165* (2013.01); *A61B 5/4803* (2013.01);
(Continued)

(58) Field of Classification Search
CPC ......... A61B 5/4824; A61B 5/11; A61B 5/165; A61B 5/4803; A61B 5/4815;
(Continued)

(56) References Cited

U.S. PATENT DOCUMENTS

| 6,757,558 B2 | 6/2004 | Lange et al. |
| 7,226,426 B2 | 6/2007 | Thomson |

(Continued)

OTHER PUBLICATIONS

David M. Hallman et al., Changes in physical activity and heart rate variability in chronic neck-shoulder pain: monitoring during work and leisure time, Int. Arch. Occup. Environ. Health, Oct. 2014, pp. 735-744, 87(7).

(Continued)

*Primary Examiner* — Catherine Voorhees
(74) *Attorney, Agent, or Firm* — Brian Kolkowski

(57) ABSTRACT

The present invention relates to systems, devices and methods for acquiring, measuring, monitoring, processing and analyzing physiological signals. More particularly, the present invention relates to using physiological signals to determine a subject's response to various conditions, variables or constraints. Still more particularly, the present invention relates to monitoring the subject's external body motion and/or environmental factors and determining the amount of pain a subject is suffering as a result of the motion and factors. Still more particularly, the present invention relates to a system, device and methods of quantifying a subject's pain to provide an objective measurement of the subject's pain. The present invention further relates to establishing and improving pain management protocols and therapy or treatment for the subject's pain based on the quantified pain measurement.

20 Claims, 9 Drawing Sheets

(51) Int. Cl.
*A61B 5/16* (2006.01)
*A61M 5/172* (2006.01)
*A61N 1/36* (2006.01)

(52) U.S. Cl.
CPC .......... *A61B 5/4815* (2013.01); *A61B 5/4839* (2013.01); *A61B 5/4848* (2013.01); *A61B 5/7278* (2013.01); *A61M 5/1723* (2013.01); *A61N 1/36071* (2013.01); *A61N 1/36139* (2013.01)

(58) Field of Classification Search
CPC ... A61B 5/4839; A61B 5/4848; A61B 5/7278; A61B 5/07; A61M 5/1723; A61N 1/36071; A61N 1/36139
See application file for complete search history.

(56) References Cited

U.S. PATENT DOCUMENTS

2002/0107434 A1* 8/2002 Lange ................. A61B 5/0478
600/301
2003/0204148 A1 10/2003 Lange et al.
2008/0249430 A1* 10/2008 John ................... A61B 5/0476
600/544
2014/0088990 A1* 3/2014 Nawana ............... G06F 19/325
705/2

OTHER PUBLICATIONS

Eric Buesher, MD et al., Improved Physical Activity in Patients Treated for Chronic Pain by Spinal Cord Stimulation, Neuromodulation, Jan. 2005, pp. 40-48, 8(1).

Zsuzsanna Kalmar et al., Effects of Spinal Cord Stimulation on Heart Rate Variability in Patients with Chronic Pain, Ideggyogy Sz., Mar. 2013, pp. 102-106, 66(3-4).

* cited by examiner

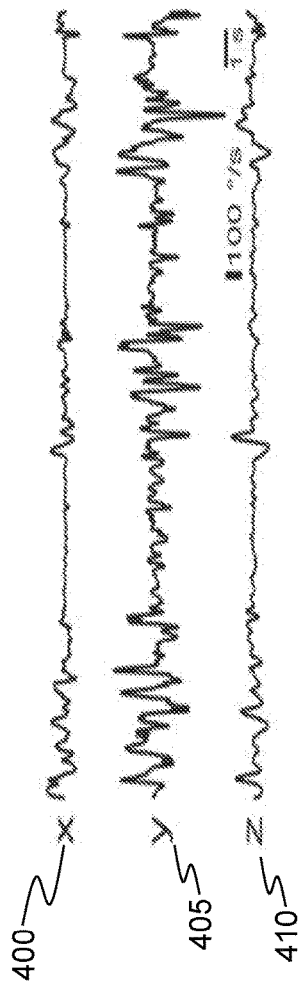

FIG. 4

| DOMAIN | OUTCOME MEASURE |
|---|---|
| Physical Activity | • Percentage of the day spent moving<br>• Relationship between active-rest periods<br>• Percentage of day in different body postures |
| Mobility and Participation | • Leg swing velocity<br>• Stride variability<br>• Double limb support time<br>• Number and duration of trips and stops<br>• Percentage of time spent at and away from home |
| Sleep Quality | • Amount of time spent asleep<br>• Number of times awoken<br>• Sleep efficiency |
| Speech | • Alternating motion rate |

FIG. 5

PAIN QUANTIFICATION AND MANAGEMENT SYSTEM AND DEVICE, AND METHOD OF USING

BACKGROUND OF THE INVENTION

1. Field of the Invention

The present invention relates to systems, devices and methods for acquiring, measuring, monitoring, processing and analyzing physiological signals. More particularly, the present invention relates to using physiological signals to determine a subject's response to various conditions, variables or constraints. Still more particularly, the present invention relates to monitoring the subject's external body motion and/or environmental factors and determining the amount of pain a subject is suffering as a result of the motion and factors. Still more particularly, the present invention relates to a system, device and methods of quantifying a subject's pain to provide an objective measurement of the subject's pain. The present invention further relates to establishing and improving pain management protocols and therapy or treatment for the subject's pain based on the quantified pain measurement.

2. Technology Review

Chronic pain affects as much as 30% of the population and is defined as pain persisting beyond a period of normal tissue healing, and/or experienced every day for 3 months or more. Chronic low back pain (CLBP) affects approximately one quarter of adults in any given year and is the most common cause of physical disability in the working population. While not a disease, people with CLBP report that most, if not all, aspects of their lives are significantly affected by their pain, and it can have a similar impact on health-related quality of life (QOL) as liver disease and cancer. Chronic pain has a significant economic impact, with an estimated health care cost of $300 billion per year. The pathophysiology of pain is not always well defined, which contributes to inconsistent patient outcomes, especially considering the reliance on patient-reported subjective outcomes. While the patient's perspective is an integral component, both treatment and research into chronic pain are greatly compromised by the fact that there is no objective diagnostic test that can complement the subjective assessment of chronic pain conditions.

Spinal cord stimulation (SCS) is the most common form of neuromodulation used in managing chronic back or leg pain, with more than 14,000 SCS implantations performed worldwide each year. SCS is a minimally invasive treatment in which electrodes are placed in the epidural space and masks pain by substituting it with paresthesia. A permanent implant is typically preceded by a trial evaluation during which the electrodes are placed percutaneously and connected to a small external stimulator. SCS has a success rate of about 50%, with sustained decreases pain intensity scores, functional improvement, and decreased medication usage. Recent evidence from off-label studies of deep brain stimulation, a more invasive form of neuromodulation, supports its use in treating forms of neuropathic pain and depression that are resistant to conventional treatments. An emerging form of neuromodulation which uses high frequency stimulation to block nerve conduction has shown promise for blocking pain transmission and is being commercialized for amputation pain. Despite these advances in the technological aspects of therapy, efficacy is universally judged by a reduction in subjective patient-reported severity, which is an important yet incomplete assessment of pain's impact on quality of life.

A number of validated tools, such as the visual analog scale and numerical rating scale and patient global impression scale, have been used to assess pain intensity. There are also a number of measures that assess the impact back pain has on function and QOL, including the pain self-efficacy scale and Oswestry disability index, but they have several limitations including: 1) they rely on self-reporting and recall, which are subjective and prone to bias, 2) they cannot be used in subjects with cognitive or communication impairments, and 3) they are not electronically time stamped and fail to capture the dynamic nature of pain and its impact on daily life.

Functional brain imaging (e.g., fMRI) has been proposed as an objective biomarker for pain intensity and perception. While imaging may eventually accurately capture pain perception, scans in the lab will not measure the effect of pain on QOL and independence, which are arguably the most important outcomes.

A number of sensors and sensing modalities are known to be useful in the measurement of pain, typically physiological signal sensors used to measure bioelectrical signals from a subject, for example EEG sensors. However, many other sensors and sensing modalities are not typically known to be useful in applications for measuring a subject's pain. For example, movement sensors such as accelerometers, gyroscopes, magnetometers, resistive bend sensors and the like, designed to measure a subject's external body motion, are not known in the art to be generally useful for measuring a subject's pain. Similarly, other sensors and sensing modalities such as audio and speech sensors, sleep sensors, video sensors, global positioning (GPS) sensors, skin conductance sensors, pulse oximeters, and even some physiological signal sensors are not generally known to be useful for pain measurement.

It is therefore an object of the present invention to: 1) effectively combine kinematic data from accelerometers and gyroscopes, and other sensor data related to physiological characteristic affected by chronic pain, with location, diary, and speech information obtained through data acquisition devices including, for example, smart phones, tablet computers, laptop computers, and the like, into a powerful research tool, and 2) provide objective measures in the clinical market to quantify and optimize therapeutic response to treatments. It is further an object of the present invention to provide accurate, objective monitoring of behavioral patterns of physical activity with sensors that may provide an accurate, objective appraisal of the impact of pain on the physical, social, and emotional functioning that complements standard patient-reported outcome measures. Given the challenges and opportunities outlined above, we aim to create an objective assessment method, system or device that will utilize motion sensors, other sensors related to physiological characteristics affected by chronic pain, GPS, and processing and interface components (such as a smart phone application, or "app") to monitor physical activity, location, and self-reported information on pain level and QOL. Still further, it is an object of the present invention that the method, system or device can be used to help manage chronic pain patients, enabling them to capture objective data related to therapeutic response. In addition to chronic pain, it is an object of the present invention that the method, system or device will have implications for other monitoring disorders (e.g., depression) that affect behavioral patterns and rely on subjective patient self-assessment. It is yet a further object of the present invention that the method, system or device could be adapted in other programs as a telemedicine platform for delivering behavioral therapy, which has been shown to be a potential mechanism for expanding health care access for pain patients.

SUMMARY OF THE INVENTION

The present invention provides dynamic assessment of the subject's physiological and environmental status. Analyses of the temporal dynamics of movement have shown that measures of the relationship between periods of rest and activity (e.g., fractal and burstiness exponents) contain clinically relevant information in both chronic pain and depression patients. This evaluation of changes in the duration of successive activity and rest periods makes intuitive sense because the duration of resting time after a physically demanding activity increases in conditions such as chronic pain and fatigue. The importance of dynamic assessment is further supported by recent studies which have demonstrated that activity fluctuations, rather than mean activity level over time, contributed significantly in explaining disability in patients with CLBP. A different dimension of motor control in speech is affected by pain, as CLBP has been demonstrated to influence speech motor rates (i.e., the rate at which syllables such as "puh" and "tuh" can be produced) independently of disability and depression. The present invention leverages the processing and interface components (e.g., smartphone microphone) to record vocal samples and quantify speech motor control. In additional to physical limitations, sleep disturbance is a common behavioral-level complaint of patients with chronic pain. Polysomnography is very useful and established for diagnosis of most sleep disorders. However, motion sensors can also be used as an effective tool for quantifying sleep. The present invention leverages the motion sensor technology to quantify and analyze a subject's sleep, particularly in relation to pain, but can also utilize traditional sleep sensors and monitoring modalities in certain embodiments. The primary focus is on use of motion sensors to obtain objective motion data which broadens the appeal of such a system because motion sensors such as accelerometers have been integrated into treatment or therapy systems such as those using neurostimulators (e.g., RestoreSensor, Medtronic) providing feedback of posture for controlling stimulation. The present invention allows for the utilization sensors in the implant of such treatment or therapy devices that allow for the capture of a comprehensive picture of motor activity, which is crucial for characterizing disability.

The present invention utilizes a device that can objectively measure various aspects or metrics from the subject and quantify a level of pain using an algorithm and data derived from the measured sensor data. The present invention integrates collection of multidimensional data and automatic report generation for tracking therapy response. The present invention utilizes multiple motion sensors, other sensors related to physiological characteristics affected by pain, GPS, and processing and interface components (e.g., smartphone application) to monitor physical activity, sleep quality, speech patterns, community mobility, self-reported patient information on pain level and quality of life. The present invention may further utilize open-loop, semi-closed-loop or closed-loop treatment or therapy delivery systems to provide treatment or therapy to the subject in light of the quantified level of pain determined by the system. In an open-loop system, or as part of a semi-closed-loop system, the subject or a third-party such as a clinician may be able to apply or administer treatment or therapy such as a pain drug or medication, for example using a portable drug titration and/or delivery device. The subject may be able to call for a bolus of pain medication on demand, but such allowances should be limited to a certain maximum dose or number of doses in order to protect the safety of the subject and to prevent over-reliance or addiction to the pain medications. Similarly, a clinician may be able to provide a dosage of drug or medication when necessary. In a semi-closed-loop system, the system may alert the user or clinician when a quantified pain level exceeds a certain threshold in order to allow the user or clinician to administer the treatment or therapy, or may provide a recommended treatment or dosage that the clinician can either confirm or override. Allowing a clinician to see, review and interact with the quantified pain levels of a subject and the treatment or therapy for the subject's pain allows the clinician to understand the particular subject's pain in a more robust way. Each subject feels and perceives pain differently, and the present invention allows the clinician the ability to understand the subject's perception in relation to the objective quantification of pain provided by the system. Such understanding allows the clinician to better understand and appreciate each subject's pain and to more accurately and effectively treat each patient. Closed-loop systems allow for the system to automatically provide tailored treatment or therapy to the subject based on the quantified level of pain, while still allowing for clinician override.

All data may be managed and processed on a secure cloud server synchronized with the smartphone app, or locally on the processing component of the method, system or device. Encrypted data may be uploaded to the server for processing whenever a mobile broadband or Wi-Fi connection is available. Reports will present changes in several behavioral-level measures, including, but not limited to: 1) percentage of day spent moving, 2) percentage of day spent in various body postures (e.g., lying, standing), 3) dynamic fluctuations in activity level throughout the day, 4) stride velocity and variability, 5) number and duration of trips away from home, 6) quality of sleep, and 7) speech alternating motion rates (AMRs). Validating these measures for pain and integrating them into a single system may provide significant differentiators between the present invention and existing commercial activity monitoring systems, with the primary innovations with unique and unexpected improvements based on algorithms and closed-loop control of therapy. Further, additional and unexpected improvements are also based on identification of physiological characteristics affected by pain, and the data acquisition sensitivity required to identify those characteristics.

The method, system or device of the present invention will utilize motion sensors, other sensors related to physiological characteristics affected by pain, and processing and interface components (e.g., smart phone application) to monitor physical activity, location, and self-reported patient information on pain level and QOL. The method, system or device of the present invention provides objective ambulatory measures of physical activity, physiological response, and community participation in patients with chronic pain. Motion sensors, other sensors related to physiological characteristics affected by pain, and processing and interface components (e.g., smart phone application) save data from the motion sensor units and log patient activity via GPS. Subjects use the interface component to enter diary information such as when they took their medications, what they were doing, or how they felt and to record vocal samples. The method, system or device then analyzes and processes the collected data to quantify response to pain therapies.

A motion sensor system or sensor unit, such as those described in U.S. Pat. No. 8,187,209, U.S. patent application Ser. No. 12/250,792, U.S. patent application Ser. No. 12/818,819, and U.S. patent application Ser. No. 13/455,423, each of which is herein incorporated by reference, may be used to acquire the various movement data. Communications for the sensor can be performed by any radio communications link known to those skilled in the art, including the preferred low-energy Bluetooth 4.0 radio or by a wired or tethered system. Using the low-energy Bluetooth radio, the device's battery will preferably last all day without needing to be recharged, and synchronization across multiple sensors is feasible. Sensor unit firmware is preferably able to communicate with the internal Bluetooth in a smartphone via the present invention's software app. The sensor board layout and housing of the motion sensor system preferably are designed and constructed so that the motion sensors and other sensors of the system can be easily worn on the wrist, torso, thigh, ankle, or any other part of a subject's body for which measurement is desired or best captured. The method, system or device may include an enclosure and strap design that utilizes a combination of elastic and rubber in the strap to maintain proper sensor alignment.

Where the present invention utilizes a smartphone and associated application ("app") for the processing and interface components, such app will preferably be available for use with any type of capable phone and operating system (e.g., Apple or Android operating systems). The app preferably includes a simple user-interface and several key features (e.g., activity monitoring via GPS, data transfer). The software preferably will take advantage of the smartphone's internal Bluetooth to collect kinematic data from the motion sensors, other sensors related to physiological characteristics affected by pain, GPS, and mobile broadband/Wi-Fi. All data is preferably encrypted. Preferably, all software and app versions adhere to recently published FDA guidance on mobile medical applications.

The software app preferably takes advantage of the smartphone's internal GPS to track where the patient travels throughout the day. Studies have shown that the more active a patient is, the better his/her QOL. The app tabulates how often the patient is at home, traveling, and at various locations. In addition to location, the app stores kinematic data from the motion sensors and other sensors related to physiological characteristics affected by pain, which will be analyzed to extract features related to physical activity. The activity monitoring feature may be designed to continuously run in the background unless disabled by the patient. The frequency of GPS tracking and communication with motion sensors and the other sensors related to physiological characteristics affected by pain (e.g., once every two minutes) will be optimized to ensure that the smartphone battery lasts for at least 18 hours.

The software app also includes a diary which patients will use to log their sleep habits, travel/activities, and self-rated disability/activity limitations. A sleep diary will be created that allows subjects to note the: 1) Type of day (e.g., work, school, day off), 2) Periods of sleep and waking, including periods of being awake at night, and 3) Consumption of coffee or alcohol. Subjects may also complete an Epworth Sleepiness Scale (ESS) or utilize other assessment methods or devices once per day to rate sleepiness. The travel log enables subjects to "check-in" at locations throughout the day, similar to functions included in social networking sites. If no entries are detected, the app may provide a cue or alarm (vibrotactile or auditory) once per hour during the day as a reminder. Self-rated pain can be entered using an 11-point numerical rating scale, similar to the current gold standard for clinical trials and pain management, which includes asking subjects to record ratings several times per day using paper forms to monitor treatment efficacy. Disability and activity limitations may be logged via subject questionnaires to be completed in the smartphone app once per day: 1), 2) the Quebec Back Pain Disability Scale to score disability, and 3) the Tampa Scale for Kinesiophobia to score pain-related fear of movement. These subject-centered manual entries of pain intensity, disability, and community mobility are used to assess the accuracy of the automatic tracking that the app performs in the background using GPS motion sensors, and other sensors related to physiological characteristics affected by pain. As a secondary outcome measure requiring minimal additional development effort, speech analysis is also integrated into the method, system or device and its software. An additional push button allows subjects to complete a syllable alternating motion rate (AMR) task, during which the syllable sequence "puh" "tuh" "kah" will be repeated as rapidly and as accurately as possible on a single breath. Chronic pain has been shown to influence speech motor rates in performance of this standardized task and built-in smartphone hardware is leveraged by the present invention for vocal quantification.

In some embodiments, subject data may be entered into a visual representation of results which, for the purposes of the present invention, is called a map. The map visually presents the quantified pain as detected, measured or otherwise determined by the method, system or device, as a result of a given set of conditions, variables or constraints. The conditions, variables or constraints may include anything which may affect the subject's pain response, including, but not limited to: movement being performed, posture, time of day, locations, position, and the like. The conditions, variables or constrains may be measured, detected or determined objectively by the method, system or device, or may be manually entered by the subject. A clinician, technician or physician may manually enter the subject's movement or physiological data into a map upon reviewing the recorded data and results, or the data may be semi-automatically or automatically entered into a map by the software of the system. The software for the system, including mapping capabilities, may be installed on and operated directly by the method, system or device, or can be web based through a web portal. The map is a tool that allows the system or a clinician, technician or physician to diagnose a subject or to determine treatment modalities or therapies to be used, or to tune therapeutic settings or parameters for a therapy device, such as a DBS device or medication infusion and/or titration device.

Preferably, the map is a two-dimensional representation of a three-dimensional graph or display of data. Generally, the horizontal and vertical axes of the map represent either individual conditions, variables or constraints, or a grouping of multiple conditions, variables or constraints. The map is then populated with quantified pain response and/or other test results obtained while the conditions, variables or constraints were affecting the subject. For example, in some embodiments, the vertical axis represents the time of day, and the horizontal axis represents the subject's posture. The map is then populated with coded indicators relating to an objective measured and quantified pain response, where the indicators may be coded by color, pattern, quantified score, or some other representation of the score or test result. Thus, if it is 2:00 AM, and the subject is in a prone position, and registers a high pain response, then the map would be populated with a high pain response marker for the given time and posture. An alternative used in many embodiments utilizes groupings of conditions, variables or constraints along one of the axes, rather than a single condition, variable or constraint. For example, the vertical axis may represent a combination of time of day and posture (e.g., axis points correlate to the time and a correlated posture measurement for that time), but now the horizontal axis may represent a measured movement (e.g., trunk rotation, perhaps indicative of the subject flipping over in his or her sleep). In such embodiments, the parameter groupings can be pre-defined sets of multiple conditions, variables or constraints, or can be combinations of pre-defined and measured conditions, variables or constraints. Therefore, instead of merely representing a single parameter, the axes may now represent groups with different combinations of conditions, variables or constraints, thus allowing for a far greater level of analysis rather than being limited to two variables. The condition, variable or constraint groupings are preferably cross-referenced within the tuning software such that the software of the system or a clinician, technician or physician can easily and quickly discern the conditions, variables or constraints comprised in each grouping. Some embodiments further allow the user, clinician, technician, or physician to add notations or comments to the map for later reference. Preferably such notations or comments are able to be toggled between visible and hidden. These maps, once populated with conditions, variables or constraints and quantified pain response results and/or other results, represent the subject's response to the various conditions, variables or constraints, or groups thereof, which contributed to the subject's pain response.

The subject's quantified pain responses are recorded in the map indicating the effect which the given set of conditions, variables or constraints had on the subject. The results that are used to populate the pain response maps may include any sort of measured, observed, or calculated response, or combinations thereof including, but not limited to, sensor recordings (for quantifying pain), patient responses and perceptions, clinician observations, and clinician scores. Preferably, subjective perception- or observation-based results are stored as annotations or notations that can be used to provide context to the conditions, variables or constraints or to the quantified, objective pain response, though some embodiments may incorporate the subjective scores into the recorded pain response. In some preferred embodiments, it is possible that the map-population process may be entirely automated such that the map is populated entirely by sensor recordings of the subject's response to the conditions, variables or constraints and no human observation or calculation is required. Thus, the maps are populated and present a potentially visible representation of much of the input and output data that the system utilizes and produces.

To minimize the data stored on subjects' phones or other processing or data acquisition device, all data may be encrypted and uploaded to a secure cloud server for storage and processing. The existing KHV stores data on an external server that provides the physical safeguards required for HIPAA compliance.

Periods of activity may be identified using the accelerometer from a motion sensor worn on the wrist, or other sensors and/or algorithms. The method, system or device, for example, extracts a measure (i.e., burstiness parameter) of the distribution of the durations of activity and rest, as this has been shown to contain clinically relevant information in chronic pain patients. Body postures (i.e., sitting, standing, lying) can be detected from the torso and thigh accelerometer signals using validated computational techniques. An appropriate filtering technique (e.g., discrete wavelet transform) is utilized to allow for detection of postural transitions. Analyzing the angular velocities recorded by the motion sensor on the shank, the method, system or device identifies important gait events such as initial/terminal contact and mid-swing. The method, system or device then estimates several temporal (gait cycle time, double support) and spatial (stride length and velocity) parameters using gait models. The method, system or device automatically extracts community mobility measures from the GPS track data. Signal processing algorithms are employed to identify the number of productions of each syllable produced in each vocal sample (i.e., alternating motion rate).

At home subjects may wear the small motion sensors, and other sensors related to physiological characteristics affected by pain, as they go about their normal routines to monitor physical activity and posture. Sensors may be worn on the wrist, torso, thigh, and ankle, or other parts of the head or body, preferably using an ergonomic form factor. The software app or software will be used to track community mobility by logging location via GPS. The wrist sensor may also be worn during sleep to monitor sleep quality. Subjects may use the processing or acquisition device, for example a smartphone app, to manually log their activities, location, and sleep habits to provide a patient-centered reference for subsequent analyses. Subjects may also use the app to record speech samples. All data may be uploaded to a web server via mobile broadband.

Algorithms automatically calculate a number of measures related to motor control, physiological characteristics and sleep quality. The time spent lying, sitting, standing, and walking, may be expressed as a percentage of the total amount of time that the sensors are worn. Double limb support time, leg swing velocity, and stride variability may be estimated from the lower extremity sensors. Sleep measures include the number of times subjects awoken during the night, the amount of time asleep, and sleep efficiency (i.e., time asleep/(total time in bed−time needed to fall asleep). The kinematic data from the wrist sensor may be used to calculate the percentage of monitoring time the subject is active and the burstiness parameter, which characterizes the dynamic pattern of activity-to-rest transitions throughout the day. The GPS data may be analyzed to identify the number of stops, number of trips, duration of stops, and length of trips. The percentage of time spent at home (i.e., within 50 m of home), in the neighborhood (i.e., within 1 km of home), in town (i.e., within 5 km of home), and out of town (i.e., 20 km and beyond from home) may also be calculated. The number of productions of each syllable may be extracted as a measure of speech motor control from each vocal sample.

The goal of the statistical analysis is to identify objective features that quantify physical activity, speech motor control, and disability. Separate one-way analysis of variance (ANOVA) calculations with Tukey post-hoc comparisons using the outcome measures above as dependent variable and the subject group (i.e., no pain, moderate pain, or severe pain) as the independent variable can show the correlation between the variables and subject pain response. Pain level is often a significant factor ($p<0.05$) across outcome features. Time spent lying is often directly correlated with pain level, while the amount of time spent standing and walking, as well as the percentage of time active, are often inversely correlated with pain group. Sleep efficiency and the amount of time asleep are often inversely correlated with pain level, while the number of times awoken is directly correlated with pain group. Mobility measures and time spent outside of home are often inversely related to the pain group. Community mobility measures extracted from GPS to the activity and trip diary information can also be compared and demonstrate about 90% agreement between the number of trips and locations tracked. Comparisons of the sleep efficiency measures to the sleep diary entries often show that that patients reporting excessive daytime sleepiness will have significantly increased number of times awoken and lower sleep efficiencies. Comparisons of the speech AMR to pain level often show that they are inversely correlated. A pattern recognition algorithm (i.e., linear discriminant analysis) can be trained to classify subjects into the pain groups using the objective measures as inputs.

A number of embodiments of the present invention are envisioned in this disclosure. The following are examples of these embodiments but in no way limit the numerous other embodiments that are encompassed by this patent application.

One embodiment of the present invention includes a portable pain measurement and quantification device or system comprising at least two sensors, each having a signal, at least one sensor adapted to measure a subject's external body movement or motion or a physiological signal associated with external body movement or motion, and at least one sensor adapted to measure the subject's speech, a processor with an algorithm adapted to receive the signals from the at least two sensors and calculate a quantified pain level based at least in part on the measured external body movement or motion and at least in part on the measured speech of the subject, and an output device adapted to output the quantified level of pain.

Another embodiment of the present invention includes a portable pain measurement and quantification device or system comprising at least two sensors, each having a signal, each sensor adapted to measure a separate physiological signals related to a level of pain of a subject, a processor with an algorithm adapted to receive the signals from the at least two sensors and calculate a quantified pain level based at least in part on the two separate physiological signals related to a level of pain of the subject, and an output device adapted to output the quantified level of pain.

Yet another embodiment of the present invention includes a portable pain measurement and quantification device or system comprising at least two sensors, each having a signal, at least one sensor adapted to measure a subject's external body movement or motion or a physiological signal associated with external body movement or motion, and at least one sensor adapted to measure a response of the autonomous nervous system of the subject to the subject's external body movement or motion, a processor with an algorithm adapted to receive the signals from the at least two sensors and calculate a quantified pain level based at least in part on the measured external body movement or motion and at least in part on the measured autonomous nervous system response of the subject, and an output device adapted to output the quantified level of pain.

Still another embodiment of the present invention includes a method of quantifying a level of a subject's pain and treating the subject's pain comprising steps of providing a portable pain measurement and quantification device to a subject, the pain measurement and quantification device comprising at least two sensors, each sensor having a signal, at least one sensor adapted to measure the subject's external body movement or motion or a physiological signal associated with external body movement or motion, and at least one sensor adapted to measure the subject's speech, a processor, a pain treatment or therapy device, and an output device, measuring with the at least two sensors a first external body movement or motion of the subject and the subject's speech, providing pain treatment or therapy to the subject, measuring with the at least two sensors a second external body movement or motion of the subject and the subject's speech, calculating with a processor two quantified pain levels of the subject, a first quantified pain level based on the first measured movement or motion and speech of the subject, and a second quantified pain level based on the second measured movement or motion and speech of the subject, determining whether the provided pain treatment or therapy needs to be adjusted based on the first and second measured movement or motion and speech of the subject, and outputting via the output device at least the determination of whether the pain treatment or therapy needs to be adjusted.

Yet even another embodiment of the present invention includes a method of quantifying a level of a subject's pain and treating the subject's pain comprising steps of providing a portable pain measurement and quantification device to a subject, the pain measurement and quantification device comprising at least two sensors, each having a signal, each sensor adapted to measure a separate physiological signals related to a level of pain of a subject, a processor, a pain treatment or therapy device, and an output device, acquiring with the at least two sensors a first measurement of the separate physiological signals related to a level of pain of the subject, providing pain treatment or therapy to the subject, acquiring with the at least two sensors a second measurement of the separate physiological signals related to a level of pain of the subject, calculating with a processor two quantified pain levels of the subject, a first quantified pain level based on the first measurement of the separate physiological signals related to a level of pain of the subject, and a second quantified pain level based on the second measurement of the separate physiological signals related to a level of pain of the subject, determining whether the provided pain treatment or therapy needs to be adjusted based on the first and second measurements of the separate physiological signals related to a level of pain of the subject, and outputting via the output device at least the determination of whether the pain treatment or therapy needs to be adjusted.

Still yet another embodiment of the present invention includes a method of quantifying a level of a subject's pain and treating the subject's pain comprising steps of providing a portable pain measurement and quantification device to a subject, the pain measurement and quantification device comprising at least two sensors, each having a signal, at least one sensor adapted to measure a subject's external body movement or motion or a physiological signal associated with external body movement or motion, and at least one sensor adapted to measure a response of the autonomous nervous system of the subject to the subject's external body movement or motion, a processor, a pain treatment or therapy device, and an output device, acquiring with the at least two sensors a first measurement of the subject's external body movement or motion or a physiological signal associated with external body movement or motion and a first measurement of the response of the autonomous nervous system of the subject to the subject's external body movement or motion, providing pain treatment or therapy to the subject, acquiring with the at least two sensors a second measurement of the subject's external body movement or motion or a physiological signal associated with external body movement or motion and a second measurement of the response of the autonomous nervous system of the subject to the subject's external body movement or motion, calculating with a processor two quantified pain levels of the subject, a first quantified pain level based on the first measurements, and a second quantified pain level based on the second measurements, determining whether the provided pain treatment or therapy needs to be adjusted based on the first and second measurements, and outputting via the output device at least the determination of whether the pain treatment or therapy needs to be adjusted.

Even still another embodiment of the present invention includes a method of quantifying a level of a subject's pain and treating the subject's pain comprising steps of providing a portable pain measurement and quantification device to a subject, the pain measurement and quantification device comprising at least two sensors, each having a signal, at least one sensor adapted to measure a subject's external body movement or motion or a physiological signal associated with external body movement or motion, and at least one sensor adapted to measure a response of the autonomous nervous system of the subject to the subject's external body movement or motion, a processor, a pain treatment or therapy device, and an output device, acquiring with the at least two sensors a first measurement of the subject's external body movement or motion or a physiological signal associated with external body movement or motion and a first measurement of the response of the autonomous nervous system of the subject to the subject's external body movement or motion, providing pain treatment or therapy to the subject, acquiring with the at least two sensors a second measurement of the subject's external body movement or motion or a physiological signal associated with external body movement or motion and a second measurement of the response of the autonomous nervous system of the subject to the subject's external body movement or motion, calculating with a processor two quantified pain levels of the subject, a first quantified pain level based on the first measurements, and a second quantified pain level based on the second measurements, determining whether the provided pain treatment or therapy needs to be adjusted based on the first and second measurements, and outputting via the output device at least the determination of whether the pain treatment or therapy needs to be adjusted.

Still yet another embodiment of the present invention includes a method of quantifying a level of a subject's pain and treating the subject's pain comprising steps of providing a portable pain measurement and quantification device to a subject, the pain measurement and quantification device comprising at least two sensors, each having a signal, each sensor adapted to measure a separate physiological signals related to a level of pain of a subject, a processor, a pain treatment or therapy device, and an output device, acquiring with the at least two sensors a first measurement of the separate physiological signals related to a level of pain of the subject providing pain treatment or therapy to the subject, acquiring with the at least two sensors a second measurement of the separate physiological signals related to a level of pain of the subject, having the subject input, via the input device, personal pain data corresponding to the subject's experiences, habits, activities or limitations encountered while the pain measurement and quantification device was measuring the subject's external body movement or motion and speech, calculating with a processor two quantified pain levels of the subject, a first quantified pain level based on the first measurement of the separate physiological signals related to a level of pain of the subject, and a second quantified pain level based on the second measurement of the separate physiological signals related to a level of pain of the subject, determining whether the provided pain treatment or therapy needs to be adjusted based at least in part on the first and second measurements of the separate physiological signals related to a level of pain of the subject and at least in part on the personal pain data inputted by the subject, and outputting via the output device at least the determination of whether the pain treatment or therapy needs to be adjusted.

Yet even another embodiment of the present invention includes a method of quantifying a level of a subject's pain and treating the subject's pain comprising steps of providing a portable pain measurement and quantification device to a subject, the pain measurement and quantification device comprising at least two sensors, each having a signal, at least one sensor adapted to measure a subject's external body movement or motion or a physiological signal associated with external body movement or motion, and at least one sensor adapted to measure a response of the autonomous nervous system of the subject to the subject's external body movement or motion, a processor, a pain treatment or therapy device, and an output device, acquiring with the at least two sensors a first measurement of the subject's external body movement or motion or a physiological signal associated with external body movement or motion and a first measurement of the response of the autonomous nervous system of the subject to the subject's external body movement or motion, providing pain treatment or therapy to the subject, acquiring with the at least two sensors a second measurement of the subject's external body movement or motion or a physiological signal associated with external body movement or motion and a second measurement of the response of the autonomous nervous system of the subject to the subject's external body movement or motion, having the subject input, via the input device, personal pain data corresponding to the subject's experiences, habits, activities or limitations encountered while the pain measurement and quantification device was measuring the subject's external body movement or motion and speech, calculating with a processor two quantified pain levels of the subject, a first quantified pain level based on the first measurements, and a second quantified pain level based on the second measurements, determining whether the provided pain treatment or therapy needs to be adjusted based at least in part on the first and second measurements and at least in part on the personal pain data inputted by the subject, and outputting via the output device at least the determination of whether the pain treatment or therapy needs to be adjusted.

Even still another embodiment of the present invention includes a portable pain measurement and quantification device or system comprising at least two sensors, each having a signal, each sensor adapted to measure a separate physiological signals related to a level of pain of a subject, a processor with an algorithm adapted to receive the signals from the at least two sensors and calculate a quantified pain level based at least in part on the two separate physiological signals related to a level of pain of the subject and to provide a recommended pain treatment or therapy protocol, an output device adapted to output the quantified level of pain, and a pain treatment or therapy device.

Yet still another embodiment of the present invention includes a method of quantifying a level of a subject's pain and treating the subject's pain comprising steps of providing a portable pain measurement and quantification device to a subject, the pain measurement and quantification device comprising at least two sensors, each having a signal, each sensor adapted to measure a separate physiological signals related to a level of pain of a subject, a processor, a pain treatment or therapy device, an output device; and a pain treatment or therapy device, acquiring with the at least two sensors a first measurement of the separate physiological signals related to a level of pain of the subject, providing pain treatment or therapy to the subject, acquiring with the at least two sensors a second measurement of the separate physiological signals related to a level of pain of the subject, calculating with a processor two quantified pain levels of the subject, a first quantified pain level based on the first measurement of the separate physiological signals related to a level of pain of the subject, and a second quantified pain level based on the second measurement of the separate physiological signals related to a level of pain of the subject, determining whether the provided pain treatment or therapy needs to be adjusted based on the first and second measurements of the separate physiological signals related to a level of pain of the subject, determining a pain treatment or therapy protocol based at least in part on the first and second quantified levels of pain and at least in part on the determination of whether the provided pain treatment or therapy needs to be adjusted, outputting via the output device at least the determination of whether the pain treatment or therapy needs to be adjusted, and adjusting the provided pain treatment or therapy according to the determined pain treatment or therapy protocol.

Even yet another embodiment of the present invention includes a method of quantifying a level of a subject's pain and treating the subject's pain comprising steps of providing a portable pain measurement and quantification device to a subject, the pain measurement and quantification device comprising at least two sensors, each having a signal, each sensor adapted to measure a separate physiological signals related to a level of pain of a subject, a processor, a pain treatment or therapy device, an output device; and a pain treatment or therapy device, acquiring with the at least two sensors a first measurement of the separate physiological signals related to a level of pain of the subject, providing pain treatment or therapy to the subject, acquiring with the at least two sensors a second measurement of the separate physiological signals related to a level of pain of the subject, having the subject input, via the input device, personal pain data corresponding to the subject's experiences, habits, activities or limitations encountered while the pain measurement and quantification device was measuring the subject's external body movement or motion and speech, calculating with a processor two quantified pain levels of the subject, a first quantified pain level based on the first measurement of the separate physiological signals related to a level of pain of the subject, and a second quantified pain level based on the second measurement of the separate physiological signals related to a level of pain of the subject, determining whether the provided pain treatment or therapy needs to be adjusted based at least in part on the first and second measurements of the separate physiological signals related to a level of pain of the subject and at least in part on the personal pain data inputted by the subject, determining a pain treatment or therapy protocol based at least in part on the first and second quantified levels of pain, at least in part on the personal pain data input by the subject, and at least in part on the determination of whether the provided pain treatment or therapy needs to be adjusted, outputting via the output device at least the determination of whether the pain treatment or therapy needs to be adjusted, and adjusting the provided pain treatment or therapy according to the determined pain treatment or therapy protocol.

Still even yet another embodiment of the present invention includes a portable pain measurement and quantification device or system comprising at least one sensor having a signal, the sensor adapted to measure a subject's external body movement or motion or a physiological signal associated with external body movement or motion, a processor with an algorithm adapted to receive the signal from the at least one sensor and calculate a quantified pain level based at least in part on the measured external body movement or motion, and an output device adapted to output the quantified level of pain.

Yet even still another embodiment of the present invention includes a portable pain measurement and quantification device or system comprising at least one sensor having a signal, the sensor adapted to measure a subject's speech, a processor with an algorithm adapted to receive the signal from the at least one sensor and calculate a quantified pain level based at least in part on the measured speech, and an output device adapted to output the quantified level of pain.

Even yet still another embodiment of the present invention includes a

Even still yet another embodiment of the present invention includes a method of quantifying a level of a subject's pain and treating the subject's pain comprising steps of providing a portable pain measurement and quantification device to a subject, the pain measurement and quantification device comprising at least two sensors, each sensor having a signal, at least one sensor adapted to measure the subject's external body movement or motion or a physiological signal associated with external body movement or motion, and at least one sensor adapted to measure the subject's speech, a processor, a pain treatment or therapy device, and an output device, measuring with the at least two sensors at least one body movement or motion of the subject and the subject's speech, providing pain treatment or therapy to the subject, calculating with a processor a quantified pain level of the subject based on the measured at least one movement or motion and speech of the subject, determining whether the provided pain treatment or therapy needs to be adjusted based on the quantified level of pain, and outputting via the output device at least the determination of whether the pain treatment or therapy needs to be adjusted.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

BRIEF DESCRIPTION OF THE DRAWINGS

FIG. 4. Alternative display embodiment of monitoring results whereby substantially real-time gyroscope measurement signals are displayed for all three axes of gyroscope measurement.

FIG. 5. Chart presenting metrics either measured or derived by the present invention.

DETAILED DESCRIPTION OF THE PRESENT INVENTION

Figure 1:
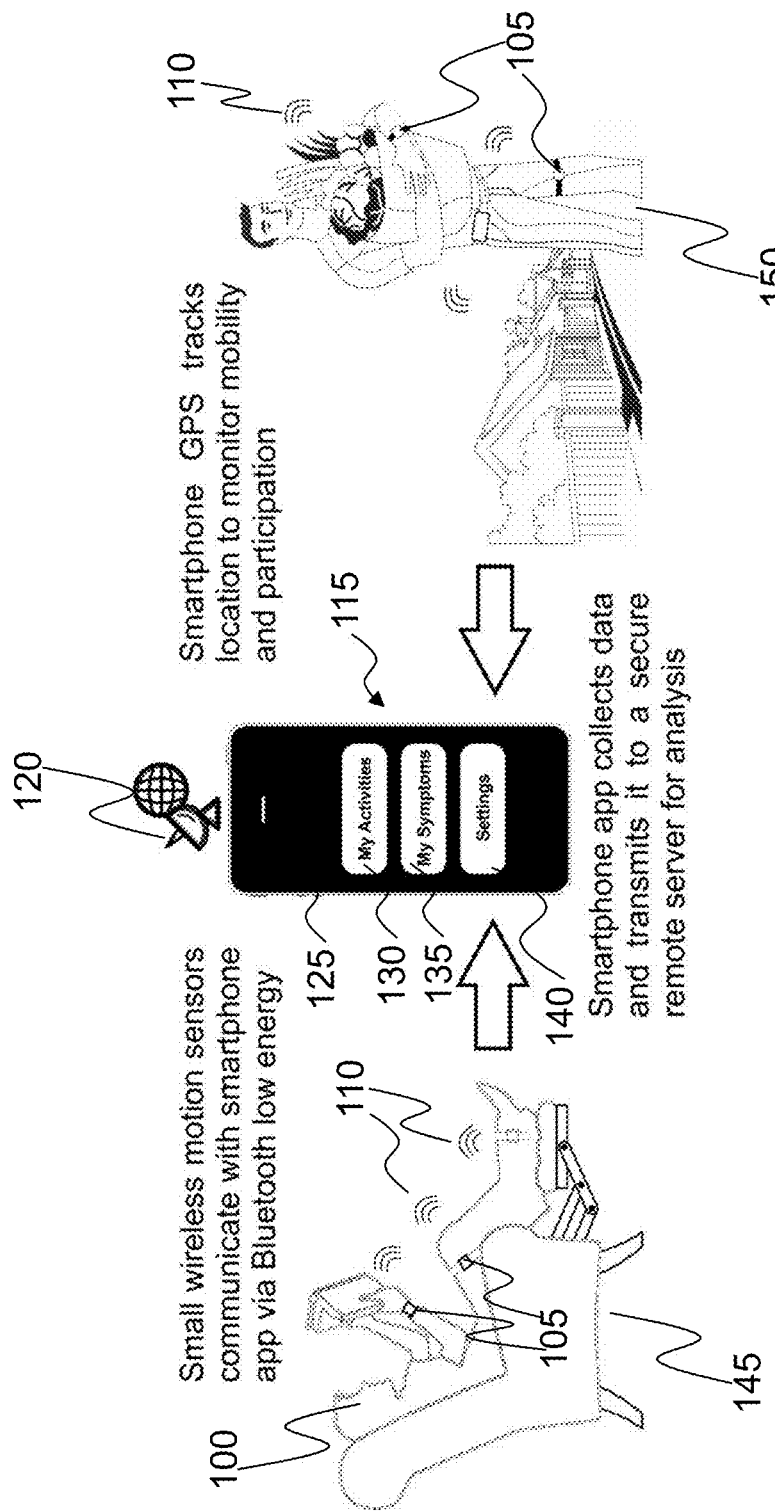
FIG. 1. Pictorial overview of one embodiment of the system of the present invention in use.

The present invention relates to systems, devices and methods for acquiring, measuring, monitoring, processing and analyzing physiological signals. More particularly, the present invention relates to using physiological signals to determine a subject's response to various conditions, variables or constraints. Still more particularly, the present invention relates to monitoring the subject's external body motion and environmental factors and determining the amount of pain a subject is suffering as a result of the motion and factors. Still more particularly, the present invention relates to a system, device and methods of quantifying a subject's pain to provide an objective measurement of the subject's pain. The present invention further relates to establishing and improving pain management protocols and therapy or treatment for the subject's pain based on the quantified pain measurement. The present invention seeks to overcome the problems and shortcomings of the current methods, system and devices in the art by providing dynamic assessment of the subject's physiological and environmental status. Analyses of the temporal dynamics of movement have shown that measures of the relationship between periods of rest and activity (e.g., fractal and burstiness exponents) contain clinically relevant information in both chronic pain and depression patients. This evaluation of changes in the duration of successive activity and rest periods makes intuitive sense because the duration of resting time after a physically demanding activity increases in conditions such as chronic pain and fatigue. The importance of dynamic assessment is further supported by recent studies which have demonstrated that activity fluctuations, rather than mean activity level over time, contributed significantly in explaining disability in patients with CLBP. A different dimension of motor control in speech is affected by pain, as CLBP has been demonstrated to influence speech motor rates (i.e., the rate at which syllables such as "puh" and "tuh" can be produced) independently of disability and depression. Thus, it is an object of the present invention to leverage the processing and interface components (e.g., smartphone microphone) to record vocal samples and quantify speech motor control. In additional to physical limitations, sleep disturbance is a common behavioral-level complaint of patients with chronic pain. Although polysomnography is necessary for diagnosis of most sleep disorders, it is also expensive, time-consuming, and interferes with sleep. Motion sensors, however, are a more cost effective tool for quantifying sleep. Further supporting the value of objective motion data, accelerometers have been integrated into neurostimulators (e.g., RestoreSensor, Medtronic) providing feedback of posture for controlling stimulation. The constraints imposed by integrating sensors into the implant (e.g., number/placement of sensors), however, prevent the capture of a comprehensive picture of motor activity, which is crucial for characterizing disability.

The devices worn by the various subjects or the different systems of the various embodiments of the present invention are preferably portable. By portable it is meant among other things that the device is capable of being transported relatively easily. Relative ease in transport means that the therapy device is easily worn and carried, generally, in a carrying case to the point of use or application and then worn by the subject without significantly affecting their range of motion or mobility. Further, portability in the sense of the present invention preferably means that all or a portion of the subject-worn monitoring device(s) is concealable and not openly visible while being worn by the subject. Furthermore, the portable pain measurement and quantification device, and optional pain treatment or therapy device preferably should be relatively light-weight. By relatively light-weight, preferably the device(s) weigh less than about 3 lbs., more preferably less than about 2 lbs., even more preferably less than about 1 lb., even more preferably less than about 0.5 lbs., still more preferably less than about 0.1 lbs., and most preferably less than about 20 grams. By being light-weight and further compact, the device(s) should gain greater acceptance for use by the subject. The entire system including the measurement and quantification device, treatment or therapy device, feedback modality, and other components including any processors, computers, video screens and the like preferably weigh less in total than about 15 lbs., more preferably less than about 10 lbs., even more preferably less than about 5 lbs., still more preferably less than about 2 lbs., and most preferably less than about 0.5 lbs. This system more preferably can fit in a reasonably sized carrying case so the subject or their caregiver can easily transport the system. Further, the portions of the device that are not worn by the subject while the device is in use should be easily and readily carryable and concealable, such as able to fit into a purse or pocket.

Another advantage of the systems and methods of the present invention is the ability to perform the measurement, analysis and quantification steps including measuring the particular metric(s) related to pain and quantifying the subject's pain, herein referred to as measurement analysis time in a very short amount of time, preferably in real-time. Preferably the system is able to measure the particular metric(s), analyze the data and provide a quantification of the subject's pain in less than 2 minutes (this can be referred to as real time measurement and quantification). More preferably, the system can measure the particular metric(s), analyze the data and provide a quantification of the subject's pain in less than 1 minute. Still more preferably, the system can measure the particular metric(s), analyze the data and provide a quantification of the subject's pain in less than 30 seconds. Yet more preferably, the system can measure the particular metric(s), analyze the data and provide a quantification of the subject's pain in less than 1 second. Even more preferably, the system can measure the particular metric(s), analyze the data and provide a quantification of the subject's pain in less than 500 milliseconds. Still yet more preferably, the system can measure the particular metric(s), analyze the data and provide a quantification of the subject's pain in less than 100 milliseconds. Even still more preferably, the system can measure the particular metric(s), analyze the data and provide a quantification of the subject's pain in less than 50 milliseconds. Yet even more preferably, the system can measure the particular metric(s), analyze the data and provide a quantification of the subject's pain in less than 1 millisecond. Most preferably, the system can measure the particular metric(s), analyze the data and provide a quantification of the subject's pain essentially simultaneously.

Still another advantage of the present invention is the ability to provide pain treatment or therapy a subject, herein referred to as pain treatment or therapy delivery time, that is similarly a very short period of time. Pain treatment or therapy delivery time refers to the amount of time it takes for the device or system to determine, based on the quantified pain level, whether the subject needs pain treatment or therapy, or needs a current level of pain treatment or therapy to be adjusted, to transmit a signal to the pain treatment or therapy device, and for the pain treatment or therapy device to administer, deliver, instruct, or otherwise provide the appropriate treatment or therapy to the subject. Preferably, the pain treatment or therapy delivery time is less than 2 minutes. More preferably, the pain treatment or therapy delivery time is less than 1 minute. Yet more preferably, the pain treatment or therapy delivery time is less than 30 seconds. Still more preferably, the pain treatment or therapy delivery time is less than 15 second. Still yet more preferably, the pain treatment or therapy delivery time is less than 2 seconds. Even still more preferably, the pain treatment or therapy delivery time is less than 1 seconds. Yet even more preferably, the pain treatment or therapy delivery time is less than 0.50 seconds. Still yet more preferably, the pain treatment or therapy delivery time is less than 0.10 seconds. Most preferably, the system is able to make the appropriate determination, transmit the signal and deliver the appropriate treatment or therapy to the subject essentially simultaneously.

Effectively, the two distinct time periods defined above are intended to operate under the real-time constraints also defined above such that the system preferably operates and performs all required steps essentially instantaneously. In light of the rapid timing of the two stages defined above, the system therefore further provides the advantage of providing pain treatment or therapy very rapidly after a measurement is taken in order to minimize the amount of time the subject suffers from the pain, and this time period is herein referred to as measurement-to-treatment time. Preferably, the measurement-to-treatment time is less than 4 minutes. More preferably, the measurement-to-treatment time is less than 2 minutes. Still more preferably, the measurement-to-treatment time is less than 1 minute. Yet more preferably, the measurement-to-treatment time is less than 2 minutes. Even more preferably, the measurement-to-treatment time is less than 30 seconds. Still yet more preferably, the measurement-to-treatment time is less than 5 seconds. Even yet more preferably, the measurement-to-treatment time is less than 3 seconds. Yet still more preferably, the measurement-to-treatment time is less than 1 second. Even still more preferably, the measurement-to-treatment time is less than 750 milliseconds. Yet even more preferably, the measurement-to-treatment time is less than 250 milliseconds. Still even more preferably, the measurement-to-treatment time is less than 50 milliseconds. Most preferably, the system measures the particular metric(s), analyzes the data to quantify the subject's pain, determines whether pain treatment or therapy is required or needs to be adjusted, transmits a signal to trigger the appropriate treatment or therapy, and provides the appropriate treatment or therapy substantially simultaneously.

The present invention is able to provide these significant improvements over systems known to those of skill in the art based on the enhanced and improved hardware and software of the present invention. The sensors utilized with the present invention are more sensitive and accurate than traditional sensors known to those in the art, allowing the system to acquire cleaner, higher quality signals and measurements directly from the subject with less noise or artifacts that need to be removed, and thus minimizing the amount of pre-processing and signal conditioning required, and time required to do so, in order to properly and effectively measure the various metrics and accurately quantify the subject's pain. Further, the processing components of the present invention are more powerful and the algorithms novel, more efficient, and better optimized, allowing the system to operate more quickly, more efficiently, and more accurately than those known in the art, further decreasing the time required to analyze the measured data, quantify the subject's pain, and administer or adjust treatment or therapy for that pain.

The devices of the various embodiments of the present invention can form part of a system for use by a physician, veterinarian, technician, clinician or therapist for therapy, treatment and further diagnosis of a subject's injury, condition, ailment or the like; for pharmaceutical research; and/or for delivery of pharmaceutical compounds or other treatment or therapeutic methods. Other elements of this system may include but are not limited to receivers, routers, communication devices, processors, displays, output devices, drug delivery devices, electrical stimulators, databases, algorithms, and the like, some of which are described further in various embodiments described in more detail below.

The preferable device or system worn, carried by or attached to the subject, contains various physiological or movement sensor(s) used to measure the subject's external body motion and/or other physiological signals from the subject's body. The subject-worn device or system may temporarily store the subject's movement or physiological data in onboard memory and/or transmit this data to an external device. In some embodiments, the subject-worn device or system may directly transmit the data to a centralized database, to multiple databases at the same or multiple locations, or to a cloud-based database where the data can be stored and accessed essentially immediately by authorized users who can analyze and/or further process the data, use it to diagnose or assess the subject's symptoms or disorders, or the like. Additionally, or alternatively, the subject-worn device or system can transmit the movement or physiological data to an external computer device, or directly to a remote location for access by a clinician, physician or technician. Transmission to a remote location preferably may include transmission directly to such a computer device at said remote location, or may involve a user (such as a clinician, physician or technician) at the remote location accessing the data or information through the database or databases as described. The computer or processor device is understood to be any type of device known to those skilled in the art usable for the intended purpose(s) or function(s), including, but not limited to, desktop computers, laptop computers, tablet computers, personal digital assistants (PDAs, "smart" cellular telephones, and the like). The computer or processor device may be provided as part of the present invention's system, but in many embodiments the movement disorder diagnostic device is designed to work with and communicate with such devices of any third-party manufacturer or provider who provides such devices for the intended function or purpose of the present invention. In such cases, a software installation providing the user interface, pain response map capabilities, diagnostic and analysis tools, and the like would simply be installed on the third-party computer or processor device as software or an application (or "app"), or the interaction with the user(s) can be web based through a web portal. The pain response map is one example of a tool that allows the clinician, physician or technician to review and/or determine the next, or preferably best (optimized) therapeutic settings or parameters for the subject's therapy device. In the present invention, pain response maps are used primarily as a tool for review and analysis of results of monitoring as well as any suggested treatment or therapy parameters or settings provided by an algorithm, and/or for full-time or regular interaction and programming by a clinician, physician or technician.

The various components of the system must be able to communicate with each other in order to transmit signals, data, commands, and the like between and amongst each other. Wireless communication is preferred for all communication of data to and from the device. Therefore, a radio or electronic component for communication is included in many embodiments of the present invention. The radio of the device controls and carries out communications between the device components, and between the portable therapy system or device and external devices. The radio may be a Bluetooth® communications device to provide wireless communications with external components such as displays, computers or processors, data acquisition circuitry, internet or cloud-based memory banks or databases, and the like, as well as internal components such as the internal portable therapy system or device memory, microprocessor, and the like. Both internal (between electrical components of the portable device) and external (between the portable device and external components or devices) communications may also be transmitted through wireless, wired, or a combination of both systems and methods. Preferably, a processor or micro-controller comprises algorithms and protocols for coordinating the operation of at least these internal electrical components, and in some embodiments also for preprocessing or processing sensor data.

Many different types and varieties of sensors can be used with the present invention to either directly acquire or measure metrics from the subject, or from whose measurements or signals other metrics may be derived. Different sensors can be used to acquire the subject's physical activity, the subject's mobility and participation in community or various activities, sleep quality, speech, or any other physiological condition of the subject. Preferably, the sensors included in the present invention are those that either directly measure physiological characteristics of the subject that are affected by pain, as well as those from which such measurements may be derived. These physiological characteristics will have either an abnormal pattern or will periodically provide an abnormal pattern which is indicative of pain intensity levels—can be suppressed, enhanced spikes, or the like. Various embodiments of the present invention may include a sensor for measuring a subject's external body motion, speech patterns, various physiological signals, and the like. The invention may also include at least one sensor for indirectly measuring movement metrics. Many types of sensors are known by those skilled in the art for measuring external body motion or providing physiological signals through which body movement information may be derived. External body motion sensors include but are not limited to accelerometers, gyroscopes, magnetometers, resistive bend sensors, combinations thereof, and the like. Preferably in some embodiments, a combination using at least an accelerometer and gyroscope is used. Sensors for acquiring physiological signals through which body movement information may be derived include, but are not limited to, electromyogram (EMG), electrooculogram (EOG), electroencephalogram (EEG), electrocardiogram (EKG), or other physiological signals which can directly or indirectly measure movement metrics in the subject, and may be included if such sensors and signals may be used to sense, detect, measure, and/or quantify the subject's external body motion, or related aspects.

One type of sensor included in many embodiments of the present invention includes gyroscopes. Gyroscopes can be used to measure, detect or otherwise determine orientation of the subject or the method, system or device. Preferably, electronic or MEMS (micro electro-mechanical system)-based gyroscopes are used. The gyroscopes of the present invention are preferably 3-axis gyroscopes, thus requiring only a single gyroscope to measure the angular momentum, and thus orientation in all three dimensions or aces rather than using three separate gyroscopes where one measures each dimension or axis. Typical gyroscopes function on the principle of the Coriolis Effect and a capacitive-based sensing system. Rotation of the sensor causes a shift in response of an oscillating silicon structure resulting in a change in capacitance. A typical application specific integrated circuit (ASIC), manufactured using a standard complementary metal oxide semiconductor (CMOS) manufacturing process, detects and transforms changes in capacitance into an analog output voltage, which is proportional to angular rate. The sensor element design utilizes differential capacitors and symmetry to significantly reduce errors from acceleration and off-axis rotations. However, in spite of the preferred characteristics, the system and devices of the present invention can operate effectively with any type of gyroscope known in the art. The preferred characteristics are such in order to aid in miniaturization and accuracy of the measurements of the system and devices, while also ensuring the most comfortable and enjoyable fit and experience for the user. Inclusion of gyroscopes in particular embodiments of the present invention, particularly in conjunction with accelerometers, allows the system and devices to detect and measure the subject's movement. Such measurements of movement aid in the tracking of health-related metrics and allow for a more robust and diverse set of data to be collected as well as derived.

Another type of sensor that can be used with the present invention includes accelerometers. Accelerometers may be used to measure determine the subject's body position and orientation. Such accelerometers may be of any type known to those skilled in the art, including magnitude accelerometers and 3-axis accelerometers. Accelerometers can be included to detect angular movements and accelerations, and the like. The accelerometers used with the present invention may optionally be a dual axis acceleration measurement system on a single monolithic integrated circuit (IC). Such embodiments may contain a polysilicon surface-micromachined sensor and signal conditioning circuitry to implement open-loop acceleration measurement architecture. For each axis an output circuit converts the analog signal to a duty cycle modulated (DCM) digital signal that can be decoded with a counter/timer port on a microprocessor. The dual axis accelerometer is capable of measuring both positive and negative accelerations. The sensor may be a surface micromachined polysilicon structure built on top of the silicon wafer. Polysilicon springs suspend the structure over the surface of the wafer and provide a resistance against acceleration forces. Deflection of the structure is measured using a differential capacitor that consists of independent fixed plates and central plates attached to the moving mass. The fixed plates are driven by 180-degree out of phase square waves. Acceleration will deflect the beam and unbalance the differential capacitor, resulting in an output square wave whose amplitude is proportional to acceleration. Phase sensitive demodulation techniques are then used to rectify the signal and determine the direction of the acceleration. The output of the demodulator drives a duty cycle modulator (DCM) stage through a 32 kOhm resistor. At this point a pin is available on each channel to allow the user to set the signal bandwidth of the device by adding a capacitor. This filtering improves measurement resolution and helps prevent aliasing. After being low-pass filtered, the analog signal is converted to a duty cycle modulated signal by the DCM stage. A single resistor sets the period for a complete cycle (T2). A 0 g acceleration produces a nominally 50% duty cycle. The acceleration signal can be determined by measuring the length of the T1 and T2 pulses with a counter/timer or with a polling loop using a low cost microcontroller. More preferably, the accelerometers are 3-axis accelerometers capable of measuring acceleration in all 3 axes.

In preferred embodiments, a single sensor unit comprising at least an accelerometer and a gyroscope may be used. More preferably, a single chip containing both a 3-axis accelerometer and a 3-axis gyroscope (e.g., Invensense MPU-6000), may be used. The sensor unit preferably not only comprises at least an accelerometer and a gyroscope, but also allows for integration of other sensors external to the sensor unit. Preferably, the accelerometer and gyroscope are each three-axis sensors capable of measuring their respective movements (acceleration and orientation) in each of the three dimensions of movement (X, Y and Z). Each of the accelerometer and gyroscope may output a separate signal for their respective measurements in each axis, and these signals are all converted from analog to digital by a bank of analog-to-digital converters (ADC). The separate ADCs for each axis of the accelerometer and gyroscope allow for simultaneous sampling of each sensor and eliminate the need for an external multiplexer. Preferably the sensor unit as a whole, and the accelerometer and gyroscope in particular are capable of operation with low power consumption. Preferably, the accelerometer and gyroscope are user-programmable such that the user may define an operating range in which the sensors will work (e.g., the accelerometer may be programmed to operate from as low as ±2 g to as high as ±16 g, and the gyroscope from as low as ±250 degrees/second to as high as ±2000 degrees/second). Some embodiments may include other sensors integrated into the sensor unit as well, for example, a temperature sensor, which may be used to monitor the temperature of the sensor unit and ensure it is operating properly and under safe conditions.

The sensor unit further preferably comprises a digital motion processor (DMP), which may perform some preprocessing or processing of the sensor signals using motion-related algorithms. The digital motion processor at least preprocesses and/or processes the accelerometer and gyroscope signals to begin the analysis of the signals and to decrease the processing load on the external processor. Many embodiments may include external or additional sensors that are not housed within the sensor unit, but whose signals are transmitted to the sensor unit for integration with the accelerometer and gyroscope signals for further transmission to other internal or external components such as a processor. Such external or additional sensors may include, but are not limited to, force sensors, magnetometers, pressure sensors, bend sensors, combinations thereof, and the like. These external or additional sensors communicate with the sensor unit by means of an auxiliary communications interface. The digital motion processor can integrate the signal(s) from these external or additional sensors along with the accelerometer and gyroscope signals and perform preprocessing or processing of all of the signals together, thus further streamlining the data acquisition process and reducing the workload of the external processor (not shown).

In many embodiments, the subject-worn device or system comprises a kinetic sensor board (or subject worn external sensor). The kinetic sensor board is preferably configured with at least an accelerometer and a gyroscope for quantifying the subject's motion. In some embodiments, the kinetic sensor board comprises at least three gyroscopes and three orthogonal accelerometers, but in more preferable embodiments the three of each sensor are replaced by at least one 3-axis accelerometer and at least one 3-axis gyroscope. The kinetic sensor board also includes a microprocessor and a power interface section.

Global positioning system (GPS) sensors may also be included on many embodiments of the present invention. GPS sensors are known in the art to be useful in tracking the subject's location, as well as distance traveled. Such measurements or determinations are useful for fitness and health applications whereby an athlete or person exercising can track his or her distance covered during exercise, and can be useful in other applications, for tracking similar values. For example, a subject wearing a device or system of the present invention can track his or her location in order to identify when the subject is at home and when the subject is away from home. By extension, the system can monitor the subject's distance traveled, as well as the time of travel, starts, stops, and the like, in order to monitor and track the subject's activity. The GPS sensors of the present invention may additionally, in some optional embodiments, be able to provide altitude measurements as well by utilizing a trilateration technique of synchronizing and measuring the distances between the method, system or device and at least four different satellites. In regards to the present invention, and particularly with respect to pain measurement and quantification, GPS data is useful in tracking the subject's movement in terms of distance, duration and starts and stops and correlating that data with the various other measures and metrics in order to assess how the subject's pain level is affecting his or her movement and involvement out in the community. For example, GPS data that indicates short distances of travel with numerous starts and stops could indicate a high level of pain as the subject has difficulty moving for longer distances or periods of time.

Another type of sensor that may be included in various embodiments of the present invention includes skin conductance sensors. Skin conductance is a measure of the electrical conductance of the skin, and is commonly known in the art as one of several names including galvanic skin response (GSR), electrodermal response (EDR), psychogalvanic reflex (PGR), skin conductance response (SCR) or skin conductance level (SCL). Galvanic skin response typically varies based on the moisture level of the subject's skin, such as is caused by sweating. Galvanic skin response can be used as an indicator of psychological or physiological stimulation or arousal—including pain. This is due to the fact that sweat is controlled by the sympathetic nervous system, which is the part of the autonomic nervous system that initiates or activates the fight or flight response in response to some stimulus applied to the sympathetic neurons. The sympathetic nervous system reacts to such stimuli by releasing acetylcholine (for preganglionic or presynaptic sympathetic neurons—those that reside in the spinal cord as part of the central nervous system (CNS)) or noradrenaline aka norepinephrine (for postganglionic or postsynaptic sympathetic neurons—those that reside outside the spinal cord, such as in the extremities, as part of the peripheral nervous system). Prolonged activation (exposure to the given stimuli) of the sympathetic nervous system can cause the release of adrenaline. The release of noradrenaline and adrenaline combine to give rise to the fight or flight response, which includes effects of increased sweating, pupil dilation, increased heart rate and increased blood pressure.

Therefore, sensors to measure galvanic skin response, as a function of the increased skin conductance caused by the increase in sweat, can be used to measure a subject's level of pain, excitement, stress, or other such indicates of psychological or physical arousal. Such galvanic skin response sensors measure the recorded electrical resistance between two electrodes when a very weak current is steadily passed between them. The sensors are normally placed a short distance apart, and the resistance recorded varies in accordance with the emotional state of the subject. Galvanic skin potential (GSP) refers to the voltage measured between two electrodes without any externally applied current, and is measured by connecting the electrodes to a voltage amplifier. Similarly, this voltage varies with the emotional state of the subject. Galvanic skin response can be highly sensitive to emotions in some people, though the GSR measurement cannot differentiate between what emotions are causing the response. GSR measurements are typically very small, such as on a microsiemen scale, but an accurately and correctly calibrated sensor and signal acquisition device or electronics can readily ascertain and measure such small values and changes in the GSR on such a scale.

Another example of the sensors that may be used in conjunction with the present invention includes a pulse oximeter. Pulse oximeters of any type known to those skilled in the art may be used. Generally, depending on the location of attachment to the subject's body, pulse oximeters tend to be either transmission or back scatter (a.k.a., reflection) sensors. Transmission sensors operate by generating a source of light at a known frequency and wavelength, passing said light through the subject's body, and measuring the amount of light that exits the subject's body on the other side. Transmission sensors, and particularly pulse oximeters, are typically applied to finger tips or the nose, generally due to the thin nature of those parts of the body as well as the ease in applying a sensor to both sides thus enabling the transmission measurement. Other areas of the body do not lend themselves as well to applying such sensors, and thus back scatter or reflection sensors may be used. Back scatter sensors operate by generating a source of light at a known frequency and wavelength, and then measuring the amount of light that bounces or reflects back to the measurement sensor which is on the same side as the light generator. These sensors tend to be less accurate than transmission sensors due to the loss of light as it scatters once it enters the subject's body—100% reflection is generally unachievable. In spite of the generally decreased accuracy, these sensors, particularly in pulse oximeters, are useful for application to the subject's ear to which would be uncomfortable and difficult to apply a transmission sensor. More specifically, with regard to the preferred sensor, the pulse oximeter can measure the oxygenation of the subject's blood by producing a source of light originating from the oximeter at two wavelengths (such as, in one embodiment, 650 nm and 805 nm). The light is partly absorbed by hemoglobin, by amounts which differ depending on whether it is saturated or desaturated with oxygen. By calculating the absorption at the two wavelengths the proportion of hemoglobin which is oxygenated can be estimated. Some embodiments, where the optional pulse oximeter is attached to or incorporated into a helmet, may be referred to as helmet-mounted pulse oximeter (HMPO) embodiments. In some embodiments, a pulse oximeter may be placed on a subject's fingertip. In other embodiments, a pulse oximeter may be placed directly on a subject's earlobe or forehead. In yet other embodiments, a pulse oximeter may be incorporated into a mask, helmet, or some other wearable, and then placed on the subject's forehead or earlobe when the mask, helmet or wearable is donned. In still yet other embodiments, a pulse oximeter may be attached in the subject's ear cup. In yet other embodiments, a pulse oximeter may be incorporated into a mask, helmet, or some other wearable, and is then placed in the subject's ear cup. In even other embodiments, a pulse oximeter may be applied to the bridge of the subject's nose, and is preferably incorporated into a mask, helmet, or other wearable. Pulse oximetry, with respect to the present invention, can provide an indication, through derivation of the pulse oximeter measurements, of abnormalities in the subject's ventilation caused by pain which lead to changes in the blood oxygen concentration Video sensors, such as cameras, video cameras, electro-optical infrared camera combinations, or the like, may be included as a sensor of various embodiments of the present invention as well. Video sensors of any variety can be used in conjunction with the present invention to provide or assist in recording pictures or video of the user and/or his or her surroundings while the method, system or device is in use, to provide movement or motion recognition (e.g., detect a subject's eye movement and adapt output or display of information based on such eye movement), or other such uses for photographic or video data recorded by such sensors. Video sensors may also be used to actually record the subject's movements in order to analyze how such movement is affected by any pain, or to even monitor the subject's facial expressions for indications of pain. All of this data can then be correlated with the other measures and metrics to help provide a quantification of pain or to populate a pain response map.

Audio sensors may be included in various embodiments of the present invention as well. A typical audio sensor may be a microphone mounted or directed towards the subject, included in an ear-worn piece such as an earbud or headset, or can be a microphone included in the processor or processing device (i.e., smartphone or tablet), or in other similar or related locations. When placed in close proximity to the subject's mouth or nose, an audio sensor or microphone can be used to record or measure several various signals or metrics. In some embodiments, such a microphone may be used for the subject to actually record audio signals such as voice notes or messages, or to interact with an external device. Additionally, a facially-oriented microphone may be used to measure a subject's breathing (i.e., breath rate or air pressure of breaths), and relatedly, snoring or other such breathing conditions. Such measurements can be used to help identify sleep cycle patterns or stages as well as be fused with other metabolic and physiological data to form a complete picture of the subjects health (e.g., breath rate during exercise may be fused with ECG and heart rate data to provide a more complete metabolic profile or cardiovascular health indication).

More preferably, audio sensors can be used to record speech patterns of the subject in order to allow those speech patterns to be analyzed in a manner to assess the subject's level of pain. There are various speech patterns that have been known to vary in accordance with the level of pain a subject is experiencing. Examples of useful and readily measurable speech patterns include specific syllables such as the "puh" and "tuh" sounds and syllables, which can be readily identified and measured using signal processing techniques known in the art. Measures or metrics pertaining to a subject's pain level that may be measured, calculated or estimated from processing and analysis of these speech patterns include sharpness or crispness of certain aspects or syllables of a subject's speech, the rate at which these discernible aspects or syllables are formed, the time it takes to form a particular aspect of speech or syllable, and the like. Depending on the particular subject and his or her response to pain, the speech patterns may vary in different ways. Some subjects may vary their speech linearly such that the subject's pain directly leads to, for example, a dulling or softening of the sharpness or crispness of a speech pattern or syllable as well as a lengthening of the time it takes to form the pattern or syllable and slowing of the rate of forming such pattern or syllable. Some speech patterns may be more robust and useful in identifying high levels of pain and others may be more sensitive to lower levels of pain. Typically, the greater the subject's pain, the more the subject's ability to form particular speech patterns is impaired. The exact combination of measures or metrics regarding speech patterns may thus be very subject-specific and therefore require calibration of the system to the particular subject's speech patterns and pain responses. In order to measure the subject's speech and use the various speech measures or metrics to help determine the subject's quantified pain level, the system must receive and record the subject's speech. The subject may be instructed to or otherwise perform a set of regimented speech exercises that direct the subject to speak certain words, phrases or syllables into the audio sensor, thus provided the system with a specific set of expected speech patterns to analyze. Alternatively, or in conjunction with instructed speech, the system may be used to measure the subject's speech either on demand whereby the subject or system initiates recording of the subject's speech, or in real-time, normal conversation or speech where the system measures whatever speech the subject happens to be engaging in. In any of these embodiments, the system records the subject's speech and performs a signal processing function to isolate the speech patterns or syllables of interest, and then processes the various measures or metrics of those patterns or syllables to help quantify the level of the subject's pain.

The system preferably is able to identify and measure the specific speech patterns in a given subject. Calibration of the system system's sensors may be required and can be performed in a number of ways. Preferably, the sensors are calibrated during a set of defined or known tasks designed to record each sensor's particular signal under the known variables to calibrate the sensor to the subject's movement. Multiple sensor measurements can preferably calibrated between and amongst each other in order to align particular pain-related responses with similar responses measured by other sensors. One example of calibration involving the speech metrics or measures preferably is performed with a regimented set of speech patterns or exercise by the subject. As the subject performs the pre-determined, regimented speech patterns, the system records the speech. This speech data can be correlated to various types of other data, both objective and subjective, in order to teach the system the correlation between the subject's measured amount of pain, perceived amount of pain and the speech pattern response. The objective calibration data may include one or more physiological signal measurements such as magnetic resonance imaging (MRI), EEG, EMG, ECG, or the like, or a combination of such signals and other measures such as described herein. For example, during a calibration session, the subject may be attached to an EEG or MRI recording device, and the subject's EEG or MRI activity measured while he or she performs the regimented calibration speech patterns. EEG or MRI data can provide an objective measure of the subject's pain level through the level of activity in the pain centers of the brain. Similarly, the patient may provide subjective data regarding is or her perceived pain level, for example using the Wong-Baker FACES scale or even mere recitation to a clinician, while performing the calibration speech. Once the calibration tasks are completed, the data can be analyzed to correlate the measured and/or subjective pain response to the change in the subject's speech patterns, and thus the system can learn how the particular subject's speech correlates to levels of pain.

With specific respect to the various speech-related measures or metrics, the system is preferably able to determine changes in the measures or metrics with a high degree of accuracy and sensitivity in order to determine even slight changes in the subject's speech that may indicate the subject is experiencing pain. With respect to the various speech patterns or syllables, preferably the system is able to detect a 75% or less variance in the time it takes to form a pattern or syllable, the sharpness of a pattern or syllable and/or the rate of forming a pattern or syllable. More preferably, the system is able to detect a 65% or less variance in the time it takes to form a pattern or syllable, the sharpness of a pattern or syllable and/or the rate of forming a pattern or syllable. Still more preferably, the system is able to detect a 50% or less variance in the time it takes to form a pattern or syllable, the sharpness of a pattern or syllable and/or the rate of forming a pattern or syllable. Yet more preferably, the system is able to detect a 35% or less variance in the time it takes to form a pattern or syllable, the sharpness of a pattern or syllable and/or the rate of forming a pattern or syllable. Even more preferably, the system is able to detect a 25% or less variance in the time it takes to form a pattern or syllable, the sharpness of a pattern or syllable and/or the rate of forming a pattern or syllable. Still yet more preferably, the system is able to detect a 20% or less variance in the time it takes to form a pattern or syllable, the sharpness of a pattern or syllable and/or the rate of forming a pattern or syllable. Yet still more preferably, the system is able to detect a 15% or less variance in the time it takes to form a pattern or syllable, the sharpness of a pattern or syllable and/or the rate of forming a pattern or syllable. Even yet more preferably, the system is able to detect a 10% or less variance in the time it takes to form a pattern or syllable, the sharpness of a pattern or syllable and/or the rate of forming a pattern or syllable. Even still more preferably, the system is able to detect a 5% or less variance in the time it takes to form a pattern or syllable, the sharpness of a pattern or syllable and/or the rate of forming a pattern or syllable. Still even yet more preferably, the system is able to detect a 3% or less variance in the time it takes to form a pattern or syllable, the sharpness of a pattern or syllable and/or the rate of forming a pattern or syllable. Yet even still more preferably, the system is able to detect a 2% or less variance in the time it takes to form a pattern or syllable, the sharpness of a pattern or syllable and/or the rate of forming a pattern or syllable. Even still yet more preferably, the system is able to detect a 1% or less variance in the time it takes to form a pattern or syllable, the sharpness of a pattern or syllable and/or the rate of forming a pattern or syllable. Detection of such degrees of variation in the given measures or metrics of speech patterns allows the system to determine that the subject's speech is becoming impaired, which may correlate to an increased level of pain.

The system preferably uses at least one of the various types of sensors described above, but may use multiple sensors, and multiple types of sensors, in many combinations to provide a more complete and robust analysis of many facets and aspects of the subject's physiological and, in some embodiments, mental states to more accurately determine the level of pain the subject is experiencing and provide a quantitative value for assessment of that pain level. Some of the described sensors may be more sensitive to actual measurement of subject pain while others may be more useful in providing other physiological or status data that can be used to calculate or estimate pain-related information. Thus, using various types of sensors, measurements and data in conjunction with each other allows the system to be better trained and calibrated to the particular user's unique pain responses, and to provide a more accurate detection or identification of actual response to pain to, in turn, provide a much more accurate quantitative pain level output.

The sensors of the present invention are preferably designed to be particularly accurate, reliable, and repeatable, and thus sensitive, in obtaining their respective measurements. Many statistical metrics can be used to evaluate the reliability and repeatability sensor measurements. Several of the most commonly used and accepted metrics include standard error of measurement (SEM), minimal clinically important change or difference (MCIC/MCID), smallest detectable difference (SDD), fluctuation, intraclass correlation (ICC), and minimal detectable change (MDC). These metrics each provide a quantitative analysis of how statistically accurate a measurement system is, and thus provide measures of the reliability, accuracy and sensitivity of these scales and systems. Methods for measuring and determining the reliability, accuracy and sensitivity of the sensor measurements, including descriptions of the metrics and their use, are described in greater detail in U.S. patent application Ser. No. 13/784,939 and U.S. patent application Ser. No. 13/785,273, which are herein incorporated by reference. As such, preferably the present invention is capable of measurements using its sensors with the same degree of sensitivity, accuracy and reliability as is described in the incorporated applications.

As noted, many embodiments of the present invention will utilize wearable sensors and, in certain embodiments, processors or processing devices. Examples of such processor or processing devices include smart phones, personal digital assistants (PDAs), laptop computers, tablet computers, personal electronic accessory devices such as watches, headphones, or the like, standalone processing devices designed specifically for use with applications of the present invention, personal fitness monitors, or the like, each embodiment including or being able to have coordinated application(s), program(s) or software installed in order to perform the analysis. The present invention preferably involves leveraging and adapting these technologies in an integrated platform with unique features to improve gait, balance, posture and movement in general or resulting from a movement disorder or disease, but also after injury (such as TBI or stroke)—a process and concept not currently known or utilized in the art. The system components provide a low-cost, portable platform that integrates sensing movement (e.g., gait patterns) and delivering cues from either or both the processor/interface/device (e.g., smart phone and associated application) and sensor(s) lends itself to many rehab and research markets stroke and TBI recovery and therapy or treatment of such injuries as well as movement disorders. The cueing device in some embodiments will provide tactile/sensory cueing on the affected body part while the subject performs activities of daily living, which commonly plays an important role and has shown success in in-clinic therapy. The small wearable profile and tactile/sensory cueing will allow the system of the present invention to be worn under clothing during the day without attracting attention that could lead to social stigma, known to discourage community use and increase abandonment of assistive technology.

The systems and methods of the present invention utilize a number of pain metrics or measures to quantify a subject's pain. These metrics or measures may be directly measured utilizing the sensors or calculated or derived from one or more direct sensor measurements. The pain metrics or measures each pertain to different aspects of the subject's physical condition and help provide the system with data that is then used to translate or correlate into a measure of the amount of pain the subject is experiencing. The pain metrics or measures can be grouped into separate families or domains based on the particular physical condition, activity or other attribute they are focused on or relevant to.

One such family or domain of metrics or measures includes those related to the subject's physical activity. Physical activity measures or metrics may include, but are not limited to, body postures and the distribution thereof, a burstiness parameter, and an overall activity level. The distribution of body postures measure is a record of the subject's body posture (e.g., seated, standing, reclined, prone, etc). Body posture can be directly measured from the sensors, typically from at least accelerometers and/or gyroscopes that may be mounted to the subject's torso. The system preferably detects and records the subject's body posture, and further preferably also the amount of time the subject spends in each different posture. The system can them calculate a percentage of time spent in each posture during the time the subject is being monitored. Another pain metric or measure related to the subject's physical activity is a parameter of burstiness. In the context of the present invention, burstiness is a measure of the dynamic relationship between periods of rest and activity. This burstiness parameter can be extracted or calculated from measures obtained by accelerometers mounted to the subject. Burstiness is thus a measurement of the increase or decrease in the subject's physical activity. Still another metric or measure related to the subject's physical activity is the subject's overall physical activity level. This measure is a cumulative measure of the subject's movement detected by the system. Typically, overall activity level can best be measured by accelerometers mounted to various parts of the subject's body including torso and limbs. From the cumulative measure of detected movement, the system can calculate the percentage of the monitoring period that physical activity was detected as well as other indications and breakdowns of the amount and type of movement or activity the subject performed, such as amount of activity using particular limbs or parts of the body.

In addition to the percentage of monitoring time that a subject spends in each postural position, the measure or metric relating to the distribution of body postures may be reported as a categorization of the subject's posture, or as a measure of the angle at which the subject's body is positioned. Preferably, the system is able to differentiate between body posture angles of at least 30 degrees. More preferably, the system is able to differentiate between body posture angles of at least 20 degrees. Yet more preferably, the system is able to differentiate between body posture angles of at least 15 degrees. Still more preferably, the system is able to differentiate between body posture angles of at least 10 degrees. Even more preferably, the system is able to differentiate between body posture angles of at least 7 degrees. Still yet more preferably, the system is able to differentiate between body posture angles of at least 5 degrees. Yet still more preferably, the system is able to differentiate between body posture angles of at least 4 degrees. Even still more preferably, the system is able to differentiate between body posture angles of at least 3 degrees. Even yet more preferably, the system is able to differentiate between body posture angles of at least 2 degrees. Most preferably, the system is able to differentiate between body posture angles of 1 degree or less. Further, while measuring the amount of change in body posture angles, the system is preferably able to detect and measure the rate at which the body posture angle is changing which may provide an indication of unsteadiness which may be caused by pain.

With respect to the metric or measure of burstiness, the system is preferably able to detect at least a 50% increase and/or decrease in the subject's physical activity. More preferably, the system is able to detect at least a 40% increase and/or decrease in the subject's physical activity. Still more preferably, the system is able to detect at least a 30% increase and/or decrease in the subject's physical activity. Yet more preferably, the system is able to detect at least a 25% increase and/or decrease in the subject's physical activity. Even more preferably, the system is able to detect at least a 20% increase and/or decrease in the subject's physical activity. Still yet more preferably, the system is able to detect at least a 15% increase and/or decrease in the subject's physical activity. Yet still more preferably, the system is able to detect at least a 10% increase and/or decrease in the subject's physical activity. Even yet more preferably, the system is able to detect at least a 7% increase and/or decrease in the subject's physical activity. Even still more preferably, the system is able to detect at least a 5% increase and/or decrease in the subject's physical activity. Still yet even more preferably, the system is able to detect at least a 3% increase and/or decrease in the subject's physical activity. Most preferably, preferably, the system is able to detect 1% or less increase and/or decrease in the subject's physical activity.

With respect to the measure or metric of overall activity level, the system is preferably able to detect at least a 50% increase and/or decrease in the subject's overall activity level. More preferably, the system is able to detect at least a 40% increase and/or decrease in the subject's overall activity level. Still more preferably, the system is able to detect at least a 30% increase and/or decrease in the subject's overall activity level. Yet more preferably, the system is able to detect at least a 25% increase and/or decrease in the subject's overall activity level. Even more preferably, the system is able to detect at least a 20% increase and/or decrease in the subject's overall activity level. Still yet more preferably, the system is able to detect at least a 15% increase and/or decrease in the subject's overall activity level. Yet still more preferably, the system is able to detect at least a 10% increase and/or decrease in the subject's overall activity level. Even yet more preferably, the system is able to detect at least a 7% increase and/or decrease in the subject's overall activity level. Even still more preferably, the system is able to detect at least a 5% increase and/or decrease in the subject's overall activity level. Still yet even more preferably, the system is able to detect at least a 3% increase and/or decrease in the subject's overall activity level. Most preferably, preferably, the system is able to detect 1% or less increase and/or decrease in the subject's overall activity level.

Another family or domain of pain metrics or measures that may be used by various embodiments of the present invention includes those metrics and measures related to a subject's mobility. Mobility is different from simple physical activity in that physical activity is a quantitative domain that pertains to the amount of movement or activity a subject performs whereas mobility relates to the subject's actual ability to perform movement or activity and is thus more of a qualitative measure. Mobility metrics or measures also can be either directly measured from one or more sensors of the system or calculated, derived or estimated from those sensor measurements. Some examples of metrics or measures that can be considered in the mobility domain include, but are not limited to, leg swing velocity, stride variability, double limb support time, and overall gait speed. Leg swing velocity is a metric or measure that measures the velocity of the subject's leg swing. Further, leg swing velocity measurements can be used to identify gait-related events, such as commencement or ending of gait activity or disturbances in gait, by using the angular velocity measurements. The angular velocity measurements obtained from gyroscopes attached to the subject's lower extremities can further be used to estimate the velocity of different shank segments during the swing phase of the subject's gait. Stride variability is another metric or measure related to the subject's mobility. Stride variability also can be used to detect and identify gait-related events like gait commencement or halting or disturbances in the subject's gait using the angular velocity measurements from gyroscopes. Further, stride variability metrics or measures can be used to estimate standard deviations of the subject's gait cycle for given periods of time. Double limb support time is still another metric or measure that can use angular velocity measurements obtained from gyroscopes attached to the subject's lower extremities to determine gait events, and further can be used to estimate the amount of time that a subject spends supporting himself or herself in double limb support. Overall gait speed is a measure of the subject's gait speed that can be estimated from gyroscopes attached to the subject's lower extremities.

With respect to the measure of leg swing velocity, the system is preferably able to detect changes in the subject's leg swing velocity of at least 50%. More preferably, the system is able to detect changes in the subject's leg swing velocity of at least 40%. Yet more preferably, the system is able to detect changes in the subject's leg swing velocity of at least 30%. Still more preferably, the system is able to detect changes in the subject's leg swing velocity of at least 25%. Even more preferably, the system is able to detect changes in the subject's leg swing velocity of at least 20%. Still yet more preferably, the system is able to detect changes in the subject's leg swing velocity of at least 15%. Yet still more preferably, the system is able to detect changes in the subject's leg swing velocity of at least 10%. Even still more preferably, the system is able to detect changes in the subject's leg swing velocity of at least 7%. Even yet more preferably, the system is able to detect changes in the subject's leg swing velocity of at least 5%. Still even more preferably, the system is able to detect changes in the subject's leg swing velocity of at least 3%. Most preferably, the system is able to detect changes in the subject's leg swing velocity of 1% or less.

With respect to the measure or metric of stride variability, preferably the system is able to accurately detect or measure the variability with a standard deviation of 50% or less. More preferably, the system is able to accurately detect or measure the variability with a standard deviation of 40% or less. Still more preferably, the system is able to accurately detect or measure the variability with a standard deviation of 30% or less. Yet more preferably, the system is able to accurately detect or measure the variability with a standard deviation of 25% or less. Even more preferably, the system is able to accurately detect or measure the variability with a standard deviation of 20% or less. Still yet more preferably, the system is able to accurately detect or measure the variability with a standard deviation of 15% or less. Yet still more preferably, the system is able to accurately detect or measure the variability with a standard deviation of 10% or less. Even still more preferably, the system is able to accurately detect or measure the variability with a standard deviation of 7% or less. Even yet more preferably, the system is able to accurately detect or measure the variability with a standard deviation of 5% or less. Even still more preferably, the system is able to accurately detect or measure the variability with a standard deviation of 3% or less. Most preferably, the system is able to accurately detect or measure the variability with a standard deviation of 1% or less.

With respect to the measure or metric of overall gait speed, the system is preferably able to detect at least a 50% increase and/or decrease in the subject's overall gait speed. More preferably, the system is able to detect at least a 40% increase and/or decrease in the subject's overall gait speed. Still more preferably, the system is able to detect at least a 30% increase and/or decrease in the subject's overall gait speed. Yet more preferably, the system is able to detect at least a 25% increase and/or decrease in the subject's overall gait speed. Even more preferably, the system is able to detect at least a 20% increase and/or decrease in the subject's overall gait speed. Still yet more preferably, the system is able to detect at least a 15% increase and/or decrease in the subject's overall gait speed. Yet still more preferably, the system is able to detect at least a 10% increase and/or decrease in the subject's overall gait speed. Even yet more preferably, the system is able to detect at least a 7% increase and/or decrease in the subject's overall gait speed. Even still more preferably, the system is able to detect at least a 5% increase and/or decrease in the subject's overall gait speed. Still yet even more preferably, the system is able to detect at least a 3% increase and/or decrease in the subject's overall gait speed. Most preferably, preferably, the system is able to detect 1% or less increase and/or decrease in the subject's overall gait speed.

Other measures and metrics related to less direct movement or activity domains are also used in various embodiments of the present invention. One such domain is community participation which relates to the subject's ability to carry on normal daily activities that require the subject to leave his or her home in spite of any pain experienced. The number and duration of trips and stops away from home that the subject takes is a measure or metric that can allow the system to quantify the subject's community participation and can be measured by using GPS tracking data, such as through use of the GPS on a smartphone or any other GPS sensor.

Sleep quality is yet another domain which relates to the subject's level of pain where the pain causes the subject to awaken or have trouble falling asleep. The system can measure the number of times the subject awakens and duration sleep by measuring periods of activity during sleep using accelerometer and/or gyroscope data attached to the subject's extremities or torso to determine position and movement during those periods of sleep.

Another important domain is speech, which can provide a strong indication of the presence of pain that the subject is experiencing. A particularly useful measure or metric in the speech domain is motor control rate and various derivatives or extrapolations thereof, such as the time it takes to form a particular speech pattern or syllable or the variability of pattern or syllable formation rate, and the like. Motor control rate is essentially a measure of the rate at which the subject forms a particular pattern of speech or syllable. The system, in certain embodiments and for various purposes, may allow and optionally instruct the subject to perform a single or series of speech tasks that records a series of vocal samples, for example through the use of a smartphone using an application and the phone's microphone, though other systems are also contemplated for use with such tasks. The system would then analyze the recorded vocal sample to detect the number and accuracy of productions of syllables. The number, frequency and duration of mistakes can be used to determine pain response of the subject during the task.

With specific respect to the motor control rate, or the rate at which a subject can form a particular speech pattern or syllable, the measure requires identification and detection of the discrete patterns or syllables. Preferably, the system is able to discern the rate at which the subject is able to form speech patterns of 50 syllables or less. More preferably, the system is able to discern the rate at which the subject is able to form speech patterns of 40 syllables or less. Even more preferably, the system is able to discern the rate at which the subject is able to form speech patterns of 30 syllables or less. Still more preferably, the system is able to discern the rate at which the subject is able to form speech patterns of 25 syllables or less. Yet more preferably, the system is able to discern the rate at which the subject is able to form speech patterns of 20 syllables or less. Still yet more preferably, the system is able to discern the rate at which the subject is able to form speech patterns of 15 syllables or less. Yet still more preferably, the system is able to discern the rate at which the subject is able to form speech patterns of 10 syllables or less. Even still more preferably, the system is able to discern the rate at which the subject is able to form speech patterns of 7 syllables or less. Even yet more preferably, the system is able to discern the rate at which the subject is able to form speech patterns of 5 syllables or less. Still even more preferably, the system is able to discern the rate at which the subject is able to form speech patterns of 3 syllables or less. Most preferably, the system is able to discern the rate at which the subject is able to form individual syllables.

Further, the system is preferably able to measure and detect the amount of time it takes for the subject to form each pattern or syllable.

Another speech measure or metric that can be correlated to the subject's level of pain is the sharpness or crispness of a particular speech pattern or syllable the subject forms. As noted, for signal processing purposes, individual syllables such as the "puh" and "tuh" syllables can be readily detected in many subject's speech. As the subject's pain level increases, the sharpness or crispness of these syllables tends to be dulled. Thus, the system preferably can measure the change in the sharpness or crispness of a particular pattern or syllable in order to determine whether a subject's pain is increasing (decreasing sharpness) or decreasing (increasing sharpness). Therefore, the system is preferably able to detect at least a 75% change in the sharpness or crispness of a particular speech pattern or syllable. More preferably, the system is able to detect at least a 60% change in the sharpness of a particular speech pattern or syllable. Yet more preferably, the system is able to detect at least a 50% change in the sharpness of a particular speech pattern or syllable. Still more preferably, the system is able to detect at least a 35% change in the sharpness of a particular speech pattern or syllable. Even more preferably, the system is able to detect at least a 25% change in the sharpness of a particular speech pattern or syllable. Still yet more preferably, the system is able to detect at least a 15% change in the sharpness of a particular speech pattern or syllable. Yet still more preferably, the system is able to detect at least a 10% change in the sharpness of a particular speech pattern or syllable. Even still more preferably, the system is able to detect at least a 7% change in the sharpness of a particular speech pattern or syllable. Even yet more preferably, the system is able to detect at least a 5% change in the sharpness of a particular speech pattern or syllable. Still even more preferably, the system is able to detect at least a 3% change in the sharpness of a particular speech pattern or syllable. Most preferably, the system is able to detect 1% or less change in the sharpness of a particular speech pattern or syllable.

Still another domain of metrics or measures are those related to autonomic tone and heart rate variability. Autonomous system time domain variability metrics or measures are typically based on physiological signals, for example those based on the beat-to-beat intervals of the subject's heart rate and include standard deviation of the beat-to-beat intervals, proportion of successive intervals that differ my more than a predetermined threshold of time, and standard deviation of successive differences in beat-to-beat intervals. Any physiological signal that provides information as to the subject's autonomic physiological response to stimuli, such as pain, may be used with the present invention to provide at least one metric or measure pertaining to the subject's level of pain. Examples of such physiological signals may include electroencephalogram (EEG) which may show the subject's brain-wave response, electrocardiogram (EKG or ECG) which may show the subject's cardiovascular response, electromyogram (EMG) which shows the electrical activity related to muscle movement, magnetic resonance imaging (MRI) which can be used to form images of the subject's body which can provide information as to its physiological state alone or in conjunction with other signals and measures described herein, and the like. Each of these physiological signals varies over time and provides an indication of the physiological status of the subject's body, and thus can be used to track how the subject is responding to stimuli, which may include pain. Other physiological signals may be directly measured or derived from these signals. One particularly important measure or metric is the subject's heart rate. Changes in a subject's heart rate, which may be measured or derived from EKG signals, may be indicative of a subject's pain response. Rapid increase in the heart rate, in particular, may indicate a sudden onset of pain, whereas elevated but somewhat stable heart rate may indicate the occurrence of chronic persisting pain. Another metric or measure that often is linked closely with heart rate in terms of pain response is respiration. Increased or persistent chronic pain can similarly lead to increased respiration rates as the heart rate increases. Further still, accompanying such pain response may be an increase in perspiration which can be detected and measured with a galvanic skin response sensor. All of these responses are autonomic responses to increases in pain which can be measured by the system to determine the subject's level of pain.

Frequency domain measures or metrics also fall into this domain and involve calculation of the power of beat-to-beat variability in various frequency bands. Typically, the preferred frequency bands utilized are high frequency and or low frequency, depending on the particular embodiment, and also the ratio of the power of the two bands can be used as a separate measure or metric.

The present invention utilizes various algorithm(s) to combine, process, assess and analyze the various metrics or measures and provide output related to the metrics or measures, the subject's pain, treatment or therapy for the pain, and many other possible outputs and combinations thereof. The different algorithms may be used alone or in conjunction in order to provide various combinations of outputs that would be useful in helping detect, quantify, mitigate and treat a subject's pain. Effectively, the algorithms monitor the various measures and metrics described above related to the subject movement, and track the changes in those metrics and measures over time. Such changes in the values of the measures or metrics may be measured through normal activity of the subject providing a picture of the changes as the subject performs those normal activities, or may be measured as a response to applied or delivered therapy or treatment. As noted, the algorithms can be tailored to output data and information in numerous forms, depending on the particular embodiment of the present invention and the needs of the subject.

Some algorithm(s) may be used to process the various measures or metrics and create a pain index. A pain index is preferably a quantitative, numerical index value that provides a clear representation of the level, amount or severity of the subject's pain. The pain index can be provided according to any numerical scale (e.g., from 0 to 10, or 1-100), and can be tailored to be presented in any numerical form (e.g., whole numbers, integers, or fractional numbers). Preferably, for the sake of ease and rapid interpretation, the pain index is presented as a positive integer and the scale is adjusted to provide the amount of detail required. The algorithm may optionally employ any one, or a combination of, mathematical models currently known to those in the art, including, but not limited to linear and non-linear classification methods such as logistic regression, artificial neural networks, k-means clustering, and the like in order to analyze and process the various metrics or measures and translate them into a pain index value. One of the most useful methods is a regression model to estimate the relationships between the various metrics or measures and estimate or predict the level of pain or disability the subject is suffering based on those metrics or measures.

Other algorithm(s) may not output a numerical value representing the pain or disability level or severity, but rather may output a visual representation, or pain response map. A pain response map, described in greater detail below, is a visual representation depicting the measured or calculated values of various variables (e.g., pain metrics or measures) obtained as a result of known variables surrounding the subject's activity, state or condition. For example, if the subject is provided with a known type of therapy under known parameters, the system can measure and calculate the various metrics or measures as a result of the known therapy parameters, and populate the map with values for the metrics or measures as a result of those parameters. The pain response map thus visually depicts the values of various metrics and measures, as well as the level of the subject's pain or disability. The maps can take on any form that usefully portrays the data to a clinician or user for analysis. One preferred embodiment presents the data as follows: columns represent objectively measured, calculated or estimated metrics or measures as obtained from the sensors of the system, rows represent different variables or parameters of the subject's movement or activity such as types of therapies, therapy parameters, (e.g., drug dosage, stimulation parameters, or the like), and the individual points (intersections of column and row vertices) are somehow coded to represent the resultant pain or disability intensity, for example by color-coding, shading, pattern, or the like. Thus, for algorithms that populate a pain response map, the objectively measured metrics or measures are analyzed and processed in such a way that the resulting pain intensity is displayed visually as a map depicting multiple responses to various parameters or variables, as opposed to the sing, perhaps momentary numerical index presented by other algorithms.

An output device is also part of many embodiments of the present invention and is adapted to provide some output, feedback, information or other communication. Preferably, the output device includes at least a visual display device, and more preferably a display that also functions as a user interface, in many embodiments of the present invention. The display device may include any of smartphones, televisions, computer or laptop monitors, tablets, eyewear (e.g., eyeglasses, sunglasses, goggles, standalone devices attached to eyewear, and the like), vehicle windshield, heads up displays, projections, or any other such medium where one could reasonably expect to notice a visual indication or message displayed. Visual indicators or messages are preferably displayed in a noticeable, conspicuous manner so as to effectively notify the subject, but not in an invasive or distracting manner such that the subject's attention is completely diverted from whatever task or activity of daily living he or she is performing (e.g., driving). The visual indicator or message may take on many and various forms, including, but not limited to a representation (e.g., numerical index) of the quantified level of pain, a warning or message regarding any aspect or part of the device or use of the device (e.g., low battery, poor sensor contact or signal, loss of communication, etc.), any aspect or part of the measurement, analysis or treatment functions (e.g., treatment or therapy protocols such as stretches or exercises to alleviate pain, measurement values obtained from the sensors, an indicator that the quantified pain level has exceeded a threshold and treatment or therapy is recommended ore required, etc.), and the like. The display device may also be used to view data and to enter data into the system. For example, the display device may preferably be a smartphone wherein the screen of the smartphone can provide any of the above messages to the user or clinician, but where, for example, the user can further interact with the device to input personal pain data, or the clinician or a technician can input initial data for the system's operation. Most preferably, the display is capable of displaying multiple types and forms of data, messages, warnings and other information simultaneously and also of emphasizing certain information based on importance or potential emergency. For example, if the drug titration device is set to provide much too high of a dose, the display might flash a warning to gain a user's attention to prevent overdosing the subject. Additionally, other output devices may be used to help provide any data, message or warning, such as audio output devices to provide an audible form of the information displayed on the display.

The display device may be integrated into the portable pain measurement and quantification device, or may be separate therefrom and independent or part of another device or system, such as a computer or tablet. Wired tethering or connection to a visual display may be feasible in some embodiments, such as if the visual display is part of a video game system the subject is playing while stationary, worn on the subject such as in the form of eyewear or a heads up display, or perhaps in a vehicle—in other words only embodiments where the subject is substantially stationary and wired connections are not a hindrance or embarrassment to the subject. Even in those circumstances, however, wireless communication is still preferred when possible.

As noted above, the present invention may be used in conjunction with other treatment, therapy or assistance devices, systems and modalities, such as with deep brain stimulation (DBS) devices, trascranial direct current stimulation (tDCS) devices, spinal cord stimulation ndevices, pharmaceutical delivery devices (e.g., drug titration and delivery systems, implanted or externally worn), and other such systems and devices. Such treatment, therapy or assistance devices and/or methods are intended to be complementary, and possibly even secondary considerations to the pain measurement and quantification of the system, but to operate in a synergistic manner such that the measurement and quantification device can be used to control and complement the treatment or therapy device to best supply the proper amount, type or level of treatment or therapy to the subject. Examples of such treatment, therapy or assistance devices and/or methods include automated stimulation devices such as deep brain stimulation (DBS), functional electrical stimulation (FES devices) and spinal cord stimulation devices, and closed-loop or semi-closed loop drug or medication titration and delivery systems, each of which is described in greater detail below, or can include providing suggestions for stretches, exercises, movement, activities or other such actions the subject can perform to prevent, alleviate or otherwise address his or her pain. The main object of the present invention is to measure and quantify the subject's pain so that the subject and/or clinician can become aware of the root cause of the subject's pain and understand the exact nature thereof, and this increased knowledge and understanding can lead to a more effective and targeted approach to addressing the subject's pain. Through continuous use of the system, it is intended for the subject and clinician arrive at not only a long-term treatment plan involving passive treatments that mask reduce or minimize the subject's pain temporarily, but also to incorporate preventative and "curative" treatments and therapies that help address the root cause of the pain and thus can help to, over time, completely alleviate the subject's pain. However, it is conceivable that there may be pain and root causes thereof too severe for the subject to address merely by changing aspects of his or her movement, posture, activity, or the like. Therefore, it is very likely that numerous treatment or therapy modalities, devices, methods, or the like will be used simultaneously or at various stages in the process of the subject's treatment. In these embodiments, the included treatment, therapy or assistance device(s) would possibly only activate, or be able to activate, under circumstances where the pain is too severe or where the root cause has yet to be identified. In the case of a DBS device, the system may activate the DBS device to provide an electrical stimulus to the subject's brain in order to initiate proper movement or motion to avoid movement or motion that causes pain. DBS devices and methods such as those described in U.S. patent application Ser. No. 13/153,063, U.S. patent application Ser. No. 13/861,790, U.S. patent application Ser. No. 13/918,948, U.S. patent application Ser. No. 14/022,323, are U.S. patent application Ser. No. 14/022,376 are quite useful in light of or with the present invention, and are herein incorporated by reference. Similarly, with an FES device, the system may activate the FES device to provide electrical stimulation to a particular muscle to help the subject perform the necessary movement correction. Another implanted electrical stimulation treatment or therapy includes spinal cord stimulation devices which may be implanted in the subject to deliver electrical stimulation directly to the subject's spinal cord to alleviate chronic pain when the precise cause can be isolated and identified to be in the subject's spinal cord. A drug or medication titration and delivery system may be utilized to administer, for example, pain medication of some variety. Additionally or alternatively, treatment or therapy may be provided in the form of instructions, suggestions or other such guidance on activities, movements, exercises, stretches, or the like for the subject to perform to address causes of pain that are based in some aspect of the subject's movement, posture, motion, or the like. This type of therapy can be delivered directly to the display of the subject's pain measurement and quantification device, or any other such display, in any format that provides sufficient instruction to the subject to carry out the particularly instructed exercise, stretch, movement or correction. These devices are not intended to be an exclusive list of potential treatment, therapy or assistance devices contemplated for use with the present invention, but merely exemplary selections intended to show the type of devices contemplated for use and the manner in which they are best used in conjunction with the present invention.

Many method embodiments of the present invention include a step of providing a portable pain measurement and quantification system or device to a subject. The portable pain measurement and quantification system or device preferably, as described herein, comprises at least one sensor having a signal, a processor comprising an algorithm and an output, an output device, and in some embodiments a pain treatment or therapy device. The portable pain measurement and quantification system or device may be a single enclosure with all components embedded, integrated or otherwise contained within or attached to the single enclosure. Alternatively, the portable pain measurement and quantification system or device may comprise an electronics housing or enclosure with the at least one sensor(s) place radially on one or more parts of the subject's body and in communication, either wired or wireless, with the electronics housing or enclosure. The signal of the at least one sensor may also depend on the particular embodiment utilized. In some embodiments, the signal from the at least one sensor may be related to the subject's movement, may be related to voluntary and/or involuntary movement, and may be as specific as movement of a particular limb or portion of the subject's body, or as general as overall movement of the subject's body as a whole. In other embodiments, the signal of the at least one sensor may be related to a response of the subject's autonomous nervous system to a stimulus, such as pain, and can be of any variety discussed herein. The signal of the at least one sensor may depend on the particular sensors used (e.g., accelerometer and gyroscope as opposed to EMG electrode, GSR sensor, temperature sensor, etc.), the placement of the sensor(s), or the particular condition, movement, disorder or other such impairment that is causing the subject's pain. Similarly to the at least one sensor, the pain treatment or therapy device may also be embedded, integrated or otherwise attached to the portable pain measurement and quantification system or device or may be a separate component in communication with the electronics housing or enclosure. The exact nature of the portable pain measurement and quantification system or device depends on the particular use. By way of non-limiting example, in an embodiment used for overcome chronic back pain, the portable pain measurement and quantification system or device may include all components in a single enclosure, including at least one sensor and the pain treatment or therapy device, and might be worn discreetly about the subject's torso or abdomen attached to a strap or harness. Such a device may require at least one gyroscope and/or at least one accelerometer, which can be installed into the device enclosure of the therapy device, and the treatment or therapy device might be a cueing device or a temperature element that can provide heat or cooling to the subject, and can be similarly installed into the device enclosure, or into the strap or harness. When the system of this exemplary embodiment detects back pain of the subject based on the signals of the at least one sensor, the treatment or therapy would provide a cue for the subject to correct his or her posture (for a cueing treatment or therapy device) or provide heat, cold, or cycle between heat and cold to help ease the pain the subject is suffering. Alternatively, in another non-limiting example, the sensors may include electromyogram electrodes placed on the subject's arms or legs, or other parts of the body, to measure the muscle movement therein, and the device enclosure may be a centralized unit attached to or carried by the subject while in communication with the remote sensors. The treatment or therapy device in such example might be separate from the portable pain measurement and quantification device and take the form of a drug titration and/or delivery system. In this example, the remote sensors measure the subject's muscle movement and transmit their signals back to the device enclosure which, upon measuring and quantifying the subject's pain, triggers the drug titration and/or delivery device to provide a drug or medication to the subject to alleviate the pain he or she is suffering.

In any such embodiment of the portable pain measurement and quantification system or device must first be provided to the subject. Providing the device to the subject may require a nominal amount of training, instruction or assistance to familiarize the subject with the device and its use. Such training may occur in the clinical setting where a physician, clinician, therapist or technician guides the subject in the donning, doffing and use of the portable pain measurement and quantification system or device and the particular or various embodiments that the particular subject may utilize. Alternatively, or in addition, video, audio or telecommunication instruction may be made available to the subject such that the subject may become acquainted with, or reacquainted with, the instructions for use of the device outside of the clinical setting, and thus not requiring a special, separate clinical appointment for retraining or recollection on the use of the device. Such non-clinical instruction may be provided through video medium (e.g., DVD, video file provided through a smartphone or tablet application) provided with the device, audio recording (e.g., .mp3 format sent to subject for remote access, on the portable device itself, provided through a smartphone or tablet application), or through teleconference or video conference whereby the subject interacts directly with the physician, clinician, therapist or technician and is walked through the use and operation of the device. Such initial and ongoing training, instruction or assistance ensures that the subject is always able to safely, properly and effectively use the system.

Once the portable pain measurement and quantification system or device has been provided to the subject and the subject is comfortable and knowledgeable as to the use of the device, the subject may then utilize the system in the manner best fitting his or her particular needs, preferably as discussed and agreed upon with the physician, clinician, therapist or technician. The subject preferably is able to use the portable pain measurement and quantification system or device, including all physical and electrical parts, including donning and doffing the device and navigating any software, user interface or other interactive and/or virtual components of the system required to effectively and safely measure the subject's movement and/or other physiological signals or indicators of pain, and provide the particular desired outcome, whether it be treatment, therapy, training, or any other such output the system is able to provide.

Many embodiments of the present invention include the step of measuring some aspect, characteristic, signal or metric from the subject. The particular measurement taken is determined by the particular embodiment, and thus the particular needs of the subject and the sensors utilized with the particular embodiment. Measurements, or data acquisition, may be performed a single time or multiple times, iteratively over an extended period of time, or may even be performed substantially continuously for the entire time the subject has the device with or attached to him or her. Preferably, for all embodiments, the measurement time adheres to the above described time periods for measurement (real-time measurement and quantification), pain treatment or therapy delivery time, and measurement-to-treatment time. As noted herein, the system may be adapted to measure the subject's movement, a response of the subject's autonomous nervous system to a stimulus, particularly pain, voice or speech, physiological biopotential signals such as EMG, EEG, ECG/EKG, EOG, and the like, or any other similar metric of the subject that relates to pain or the amount of pain the subject is suffering.

For embodiments that include measuring the subject's movement, more specifically the external body movement or motion, or a physiological signal associated with external body movement or motion with the at least one sensor of the portable therapy system or device, the measurement is performed using the various sensors described herein to measure the subject's body motion. As noted, typical sensors may include at least one of, or combinations of, gyroscopes, accelerometers, EMG electrodes, magnetometers, resistive bend sensors, load cells, and the like. The various sensors can be placed on any part of the subject's body such that the sensor can measure the movement of that part of the body and effectively provide movement data that can be used to measure the subject's movement and quantify pain of the subject from those measurements. The sensors acquire their respective signals and transmit those signals to the electronic components of the portable pain measurement and quantification device. The particular transmission method determines on the format of the particular embodiment. As noted herein, some embodiments may include sensors embedded in, integrated in or attached to the device enclosure of the portable pain measurement and quantification device and thus the device enclosure would likely include internal hard-wired communication circuitry between the sensor(s) and the electronics of the device, and other embodiments may include separate, remotely-placed sensors which may utilize wires or cords to connect the sensors to the electronics in the device enclosure or, more preferably, communicate wirelessly with the electronic components. Wireless communication requires at least one electronic component for transmission of the signal from the sensor and at least one electronic component for receiving the signal by the device enclosure. Preferably, such wireless communication components are each capable of two-way communication such that the remotely-placed sensors and the electronics of the portable therapy system or device are each capable of transmitting and receiving signals and data to and from each other. This is particularly preferable for embodiments including a pain treatment or therapy device that is separate from the portable pain measurement and quantification device and local to the remote sensor locations, and thus allows the device to provide treatment or therapy directly to the particular part of the subject's body.

Preferably, the step of measuring the subject's movement is performed substantially continuously. By substantially continuously, it is meant that preferably, while the subject is wearing the portable pain measurement and quantification device, the device and its sensors effectively monitor the subject's movement constantly as opposed to taking intermittent or periodic measurements, and as opposed to only measuring during a particular task or function. This substantially continuous measurement effectively means to support real-time discreet movement measurement while the subject goes about performing activities of daily living rather than being a clinical device for measurement of measurement at predetermined times, during predetermined activities or tasks designed for clinical purposes. Instead, the portable pain measurement and quantification device of the present invention is intended to be a measurement and quantification, and preferably a therapy, training and improvement tool constantly monitoring the subject's movement to detect pain substantially as it occurs. Real-time for purposes of movement measurement is meant to fit within the preferred ranges and constraints defined above. With respect to substantially continuous measurement of the subject's movement, it is meant that preferably the sensor(s) of the portable pain measurement and quantification device acquire movement data once every 60 seconds. More preferably the sensor(s) of the portable pain measurement and quantification device acquire movement data once every 30 seconds. Still more preferably the sensor(s) of the portable pain measurement and quantification device acquire movement data once every 10 seconds. Even more preferably the sensor(s) of the portable pain measurement and quantification device acquire movement data once every second. Still yet more preferably the sensor(s) of the portable pain measurement and quantification device acquire movement data once every 0.5 seconds. Even still more preferably the sensor(s) of the portable pain measurement and quantification device acquire movement data once every 100 milliseconds. Yet even more preferably the sensor(s) of the portable pain measurement and quantification device acquire movement data once every 50 milliseconds. Even yet more preferably the sensor(s) of the portable pain measurement and quantification device acquire movement data once every millisecond. Most preferably the sensor(s) of the portable pain measurement and quantification device acquire movement data at intervals less than 1 nanosecond. Such continuous measurement intervals may, in some embodiments, also include not only acquisition and measurement of movement data but also transmission of the signal from the sensor(s) to the electronics of the portable pain measurement and quantification device.

Many embodiments of the present invention include a step of providing some variety of treatment or therapy to the subject to help alleviate, prevent or otherwise address the pain he or she is experiencing. The treatment or therapy provided can be of any type using the treatment or therapy devices or tools described herein, or those known in the art. Examples of providing treatment or therapy to the subject include providing deep brain stimulation (DBS) to the subject using a DBS device or system, providing transcranial direct current stimulation (tDCS) using a tDCS device or system, providing pharmaceutical, drug or medication treatment to the subject by either instructing or prescribing a drug or medication to the subject or using a drug or medication titration and/or delivery system, or by providing instructions or guidance on particular movements, exercises, stretches, motions, posture, or other similar guidance to the subject on how to correct or address some aspect of his or her movement or body in order to address the cause of the pain. Such instructions or guidance may be provided to the subject visually, such as on a visual display of the portable pain measurement and quantification device, or any other visual display, or audibly via speakers or headphones of any variety that project audible commands or instructions to the user. The visual instructions or guidance can take the form of text, video, animation, or any other such form of portraying instructions for the subject to perform.

The particular type or variety of treatment or therapy depends on the particular embodiment of the present invention. Regardless of the type or variety of treatment or therapy being utilized, various embodiments of the present invention employ an iterative step of providing the treatment or therapy in order to attempt to reduce or eliminate the subject's pain. Whether the treatment or therapy is effective in reducing or eliminating the subject's pain is preferably measured and determined by subsequent or successive measurements and quantifications of the subject's pain using the portable pain measurement and quantification device. Essentially, whether the sensor measurement is periodic or continuous, when an initial pain measurement and quantification leads to a determination that treatment or therapy is required, the treatment or therapy is applied, and a successive pain quantification is measured and provided. The difference between successive quantifications of the subject's pain allows the system to determine whether the applied treatment or therapy is effective in reducing or eliminating the subject's pain. The determination then allows the system whether new or additional treatment or therapy, a reduction or cessation of the applied treatment or therapy, or maintaining the same level and variety of treatment or therapy is required or likely to be beneficial to the subject.

Some embodiments of the present invention allow for the user or subject to input personal data into the device for use in the analysis or for cataloguing and notation purposes. Examples of personal data the subject may be able to enter include experiences, observations or opinions of events that occur during the monitoring period, habits or usual activities the subject tends to perform, activities or tasks performed, and limitations, hindrances, pain or other impairments experienced during such activities or tasks. Additionally, the subject may be able to input personal pain data directly related to the subject's perceived level of pain. The subject's perceived pain level and be input according to any scale chosen and set into the device. The subject may be able to enter such pain information freely on an ad hoc basis, or may be prompted to do so at various intervals or periods, or during certain events such as beginning and ending of the monitoring period. If the system prompts the subject for personal pain level input, it may be done in any manner sufficient to guide the user to select an appropriate level on the chosen scale, such as in a manner similar to the subject being presented a Wong-Baker FACES Pain Rating Scale and asked to select the face that most closely represents the perceived level of pain. Preferably, the system requires a higher level of inquiry into the subject's perceived pain level, and utilizes more in depth information relating to how the level of pain is affecting or has affected the subject's ability to perform certain tasks or activities, effectively going beyond merely the amount of perceived pain and analyzing the level of disability due to pain.

In order to allow the user to input such personal data, the system preferably includes an input device. The input device can be a separate, standalone unit or device that transmits data and information to the system, such as a computer or tablet in communication with the subject-worn system. More preferably, however, the input device is integrated into or otherwise part of the system, such as the processor or processing device. As noted above the processing device may be part of a computer or tablet, but such processors are not as readily portable for use while the subject is out performing activities, particularly in community involvement scenarios. In a preferred embodiment, the processor and input device are part of a smartphone or similar device with an accompanying application designed for the purposes of the present invention to receive input from the subject, clinician and sensors, analyze the data, and provide and output results of the monitoring and analysis. As such, the subject can utilize the input modalities of the smartphone or similar device, such as physical keyboard, on-screen keyboard, microphone, camera and video camera in order to input any information required or desired.

Many embodiments of the present invention further include a step of calculating various quantified pain levels. This step is preferably performed by an algorithm specifically designed and optimized to account for the unique and numerous metrics and inputs of the system of the present invention in order to provide an accurate and object value for the quantity of pain the subject is experiencing. The algorithm is designed to gather all subject data—either objectively measured by the device or system or subjectively input from the user or clinician—and to coordinate, weigh, and integrate all sources of data in order to calculate an objective pain quantification value. The algorithm calculates and produces a quantification of the pain that represents the subject's level of pain or the pain intensity. Based on the particular clinician and/or subject, the objective pain scale used to calculate and analyze the subject's pain can be different depending on the particular circumstances, and given that there are no generally accepted clinical object pain scales in use currently. The pain scale used can be of any cariety that can demonstrate varying levels or intensities of pain. For example, the scale may be numeric and use whole numbers or positive integers from 0-100, fractional or rational numbers from 0-10 (on any incremental scale in between such as quarter, half or tenth numbers for example), or any other numbering system the clinician or device programmer may choose. The scale may also be shade- or color-based with various pain quantifications being represented on a grey-scale (from white to black) or in color (e.g., shades of green to shades of red) to show the intensity. The quantified pain value or indication, in whatever form, is preferably output or presented to the user via the output device of the portable pain measurement and quantification device. Optionally, and in addition or alternatively, the quantified pain value may be transmitted and/or output for a clinician to see and analyze the subject's pain, and any treatment or therapy being applied.

The quantified pain level or intensity can be displayed in a manner that shows the subject's response to various treatment or therapy modalities and/or to various treatment or therapy variables or parameters. A map, or pain response map, is a two-dimensional representation of a three-dimensional set of data wherein the system can present the subject's quantified pain as a function of many variables or factors. For example, items or labels along the vertical axis may represent different treatment or therapy types or modalities (e.g., drug delivery, DBS therapy, and tDCS), or may represent different settings or levels of a particular type of therapy or treatment (e.g., different drug or medication doses of the same drug, different drugs or medications, different exercises or stretches, different DBS amplitudes). Similarly, for example, items or labels along the horizontal axis may represent different variables of the treatment or therapy or groupings thereof, such as several groups of DBS parameters where each group has at least one parameter or variable that is different from the other groups, such as the selected stimulation contact, waveform, duration, or the like. Therefore, when treatment or therapy is applied according to the variables or factors indicated on the vertical and horizontal axes, the system can measure and quantify the level or intensity of pain the subject experiences in light of the treatment or therapy, and populates the point of intersection with the quantified pain level or intensity. Such a map allows the user, and more importantly a clinician, to see exactly which treatment or therapy and the settings, parameters or variables are the most effective in alleviating the subject's pain. This map system allows for tailored and targeted treatment or therapy based on objective, quantitative data rather than merely relying on observation of the subject or the subject's self-reported level or intensity of pain.

Another step in many method embodiments of the present invention is determining whether the treatment or therapy needs to be changed, adjusted, or altered in any way. By performing the iterative measurement and quantification of pain as described above, the system can populate the map, or pain response map, in order to show the subject's response to various forms and variables of treatment or therapy. This not only provides the clinician or system with an optimal or most effective treatment or therapy plan, but it also clearly demonstrates the treatment or therapy that is almost as effective as the optimal combination. Therefore, when the subject is receiving a prescribed treatment or therapy and the system measures and quantifies an increased level or intensity of pain, or simply a quantified level or intensity of pain that is not expected based on the applied treatment or therapy, the system or a clinician can then determine that the treatment or therapy is not presently effective, and that the treatment or therapy needs to be changed, adjusted, or otherwise altered. The benefit of the pain response map is that set of "next best" treatment or therapy alternatives is known and available and allows the system to intelligently select the next treatment or therapy, and the parameters thereof, to apply. This significantly reduces the amount of time the subject likely has to suffer from the increased or altered pain and allows the system to rapidly adapt to the subject's changed pain condition.

Another step in many method embodiments of the present invention is that of outputting the determination(s) of the algorithms for use by the subject, a clinician, or another device. The determinations may be one or more of those discussed herein, including data for storage and/or review, a quantified pain index, a visual pain response map, various warnings or messages, or commands or controls for other systems or devices such as treatment or therapy devices. The step of outputting the determination, then, depends on the particular embodiment. Data for storage and/or review is preferably output by transmitting the data to device or remote location intended for storage of the data and for retrieval by the subject or a clinician when necessary or desired for review. Quantified pain indices are preferably output both to a display device and stored over time. The pain index display allows the subject or clinician to see the estimated level of pain on a real-time basis, either through a continuous display or on demand (e.g., the system utilizes a smartphone for continuous monitoring and the user can turn on the smartphone display to see the pain index). The pain index could also be output audibly such as by an auditory recitation of the actual index value, or by any variety of audible sound to indicate that the pain index has changed or perhaps reached some threshold related to a pain level of interest to the subject or a clinician. Similarly, the pain response map may be output to any visual display device such as the integrated or connected processor device (e.g., smartphone) or may be transmitted to a separate and/or remote display device such as a computer or tablet. By the very nature of the information displayed in the pain response map, the most preferable output of the map is to a device where the clinician can review and analyze the subject's pain response and determine an appropriate course of action, treatment or therapy to help reduce, mitigate and alleviate the subject's pain. Warnings or messages can be output visually (e.g., flashing lights or screens, changing colors, text messages across a visual display, or the like), audibly (e.g., audible tones, notes or tunes akin to notifications from a cellular phone, spoken messages, or the like), through tactile notifications (e.g., vibration), or any other method of alerting or notifying the subject or clinician of a condition or event requiring attention. The system further can output commands or controls for other devices such as treatment or therapy devices, particularly where for systems utilizing semi-closed-loop or closed-loop control. In these embodiments, the system may output recommended treatment parameters or protocols and allow the subject, or more preferably, a clinician to review, edit and/or approve the parameters or protocols so that the treatment or therapy device may administer the treatment or therapy to the subject. Such output may include a pain response map as well as recommended parameters, but may just include treatment parameters while allowing for the option to selectively view actual measurement data to confirm that the recommended settings are acceptable or need to be edited. Alternatively, particularly in closed-loop systems, the processor device may directly transmit treatment or therapy parameters or settings to the treatment or therapy device such that the parameters or settings are programmed into the treatment or therapy device such that the device then operates to provide treatment or therapy to the subject based on the newly programmed parameters or protocol.

The semi-closed-loop or closed-loop treatment or therapy embodiments of the present invention can either utilize the local processor device or a remote processor device to suggest and provide recommended or automated treatment or therapy parameters or protocols. In such embodiments, at least one electronic component for transmitting and receiving signals is required. The subject-worn monitoring device needs to have at least one electronic component for transmitting signals and data, particularly programming commands comprising treatment or therapy protocols, and the treatment or therapy device must have at least one electronic component for receiving such signals and data. In such embodiments, data corresponding to the subject's measured and calculated metrics and measures and resulting pain analysis data may be collected by the subject-worn monitoring device and transmitted using the at least one electronic component for transmitting signals either directly to the treatment or therapy device (closed-loop systems) or to a remote location or remote locations for review and analysis by a clinician, physician or technician (semi-closed-loop or open-loop systems). The data may be transmitted to a clinical center or location where a clinician, physician or technician can view the data. In such embodiments, the clinician, physician or technician can then make a decision and determination regarding a level of treatment or therapy parameters or settings that should be applied to the subject's therapy device. Alternatively or in addition, an algorithm may be used to provide the determination as to the level of therapy parameters to be applied to the subject's therapy device, and a clinician, physician or technician may optionally review the settings determined by the algorithm. In some embodiments utilizing remote adjustment of therapy or treatment, once a determination as to level of treatment or therapy parameters or settings is made, this level of parameters or settings is then transmitted back to the subject's therapy device where it is received by at least on electronic component for receiving signals. In still other remote embodiments the subject-worn monitoring device may provide a suggested or determined level of therapy parameters, and in such embodiments the movement data and/or such suggested or determined treatment or therapy parameters or settings may be transmitted to the treatment or therapy device to automatically program the treatment or therapy device to operate according to the parameters or settings. Additionally, the movement data and/or level of treatment or therapy parameters or settings may additionally be transmitted to a remote location for review and/or storage, and/or a central server, cloud based server, or other such database for storage and backup purposes.

Once suggested treatment or therapy parameter or setting adjustments are computed by the treatment or therapy computation algorithm(s), the adjustments or new parameters or settings may optionally be displayed on a display or user interface of a local or remote processing device or system. A treatment or therapy algorithm of the processor or processing device then computes suggested therapy device parameters or settings based at least in part collected movement data comprising the measured or calculated metrics or measures and/or the resulting output of the system regarding pain quantification, for example quantified pain index or the pain response map produced from the measures or metrics. Other input that may necessarily be included in the determination of therapy or treatment parameters or settings includes previously set treatment or therapy parameters that have been applied to the subject. This is particularly relevant for embodiments utilizing the pain response map which may include as an input current therapy or treatment parameters or settings and which then tracks the subject's pain response to those parameters or settings and attempts to offer new parameters or settings that better alleviate the subject's pain. In many embodiments, the various algorithms utilized are able to analyze the measured and quantified movement and pain data in correlation to the therapy parameters or settings being provided, determine if those parameters or settings are adequately addressing the subject's needs, and be able to adjust the parameters or settings to better address the subject's needs. In such embodiments, the algorithm would then know to avoid the parameters or setting that are likely to not adequately address the subject's pain, and thus avoid including them in the provided set or group of parameters and settings.

Referring to the drawings, FIG. 1 presents a pictorial overview of one embodiment of the system of the present invention in use by a subject. The particular embodiment depicted utilizes motion sensors 105, other sensors related to physiological characteristics affected by pain (not shown), GPS 120, and a smart phone 115 application (i.e., "app") 125 to monitor physical activity, location, and self-reported information on pain level and QOL. The depicted embodiment of the smartphone app shows a user interface which allows the subject to enter or review data corresponding to the activities 130 he or she has performed or is performing, the symptoms 135 her or she exhibits in the measured movement which may contribute to or cause pain or other disability, and general settings 140 for the app and system. Whether the subject 100 is at rest 145 or performing some activity, movement or motion 150, the sensors 105 can be worn, attached to, or carried by the subject 100 to continuously acquire signals to monitor the subject's physiological status. The sensor(s) 105 are preferably small and wireless, though wired embodiments may be preferable for some applications. The sensors 105 may include motion or physiological sensors to measure and monitor the actual movement or condition of the subject 100, or environmental sensors, such as GPS 120, to determine the subject's location and overall activity. The sensors 105 preferably communicate 110 with the processing device, in this embodiment a smartphone 115 with an associated app 125, and the smartphone 115 and app 125 collect, process and analyze the data. The analyzed data can be organized and/or presented in many different ways, and can optionally be transmitted to a remote, secure location or server (not shown) for further analysis.

Figure 2:
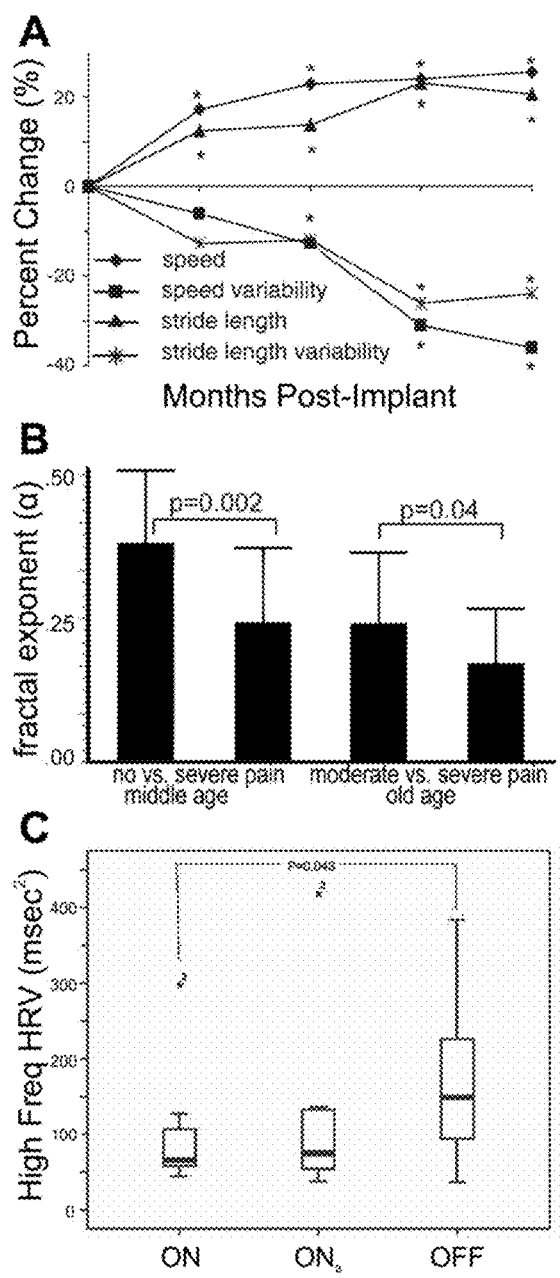
FIG. 2. Graphical depiction of various clinically observed or measured metrics or analytical data processing values in an experimental group, such metrics being able to be measured by the present invention objectively, such measures or analyses including: (A) percent change in pain intensity over time after treatment or therapy, (B) fractal exponent characterization of subject pain, and (C) heart rate variability measurements compared with therapy or treatment on or off.

FIG. 2 depicts graphical trends of results for various metrics that show improvement over time in subject pain perception after implantation of an electrical impulse generator system, such as a spinal cord stimulation system. Specifically, the graphs show (A) percent change from baseline before implant to 12 months after SCS implant in self-rated pain intensity—a subjective grading value provided by the subject based on perceived pain, (B) a fractal exponent metric or measure used to characterize subtle differences in subject's with chronic pain as a result of the high degree of sensitivity of the sensors and system, and (C) a heart rate variability measure or metric of a subject. The motion-sensor measured metrics depicted are merely examples of metrics which can be used to objectively and accurately measure and monitor the subject's pain level in order to ensure that proper and optimal treatment and therapy is being provided to the subject. These graphs depict improvements of a subject over time as a result of treatment or therapy and monitoring of the subject's pain and the sensitivity of the various sensors and the system as a whole.

Figure 3:
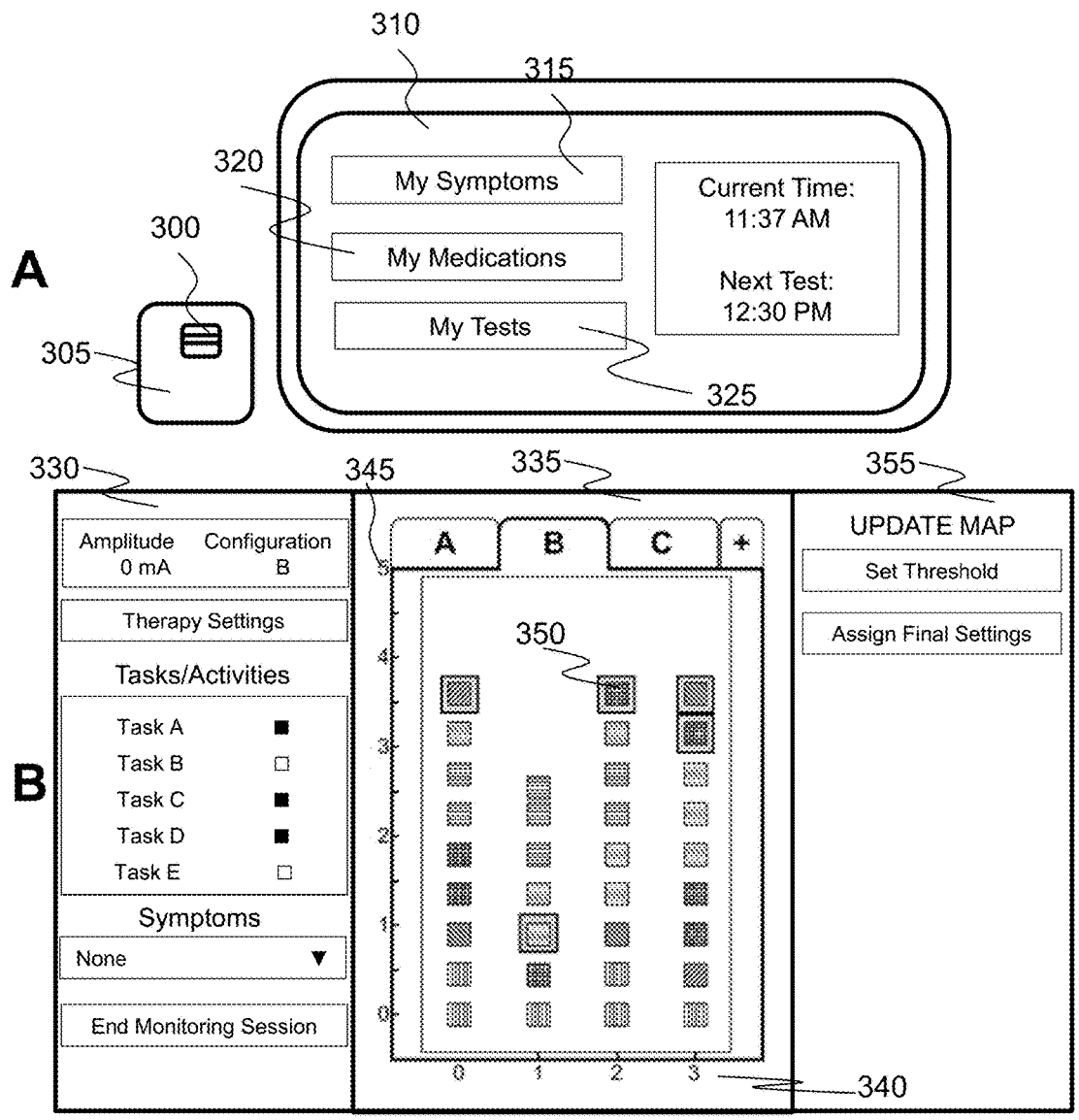
FIG. 3. Depiction of various components of the system and device of the present invention, including: (A) sensor unit and processing device, and (B) software/user interface and monitoring results.

FIG. 3 depicts various aspects of the device or system of the present invention. FIG. 3 A depicts an example of a subject-mountable sensor unit 300 on top of a charging pad 305 that can be used to charge the sensor unit's internal batteries via an induction charging process. The charging pad 305 may, in some embodiments, additionally provide a cue to initiate data transmission from the sensor device to a processing device and/or a remote location or server. Alternatively, such data transmission may be automatic and/or continuous. The system further includes a processing device 310, which is depicted as a tablet computer 310 in the present embodiment. However, the processing device can be any variety of device capable of processing data and running associated software for proper data analysis. Examples of such devices may include tablet computers, laptop computers, desktop computers, personal digital assistants (PDAs), standalone specialty processing devices, smartphones, smart watches, and the like. The specific embodiment depicted in (A) includes a subject-mountable sensor unit 300 that contains three-axis accelerometers (not shown) and gyroscopes (not shown), and a Bluetooth radio (not shown). In some embodiment, instructional videos on a tablet 310 may guide subjects through a motor exam. All data is uploaded from the tablet 310 to a secure HIPAA compliant server (not shown). In the depicted embodiment, the tablet is displaying a user interface whereby the subject can interact with the app or software in order to input, review, or edit various sets of data including a list of symptoms 315 that the system has determined to be present from the various metrics and measures, a list of medications 320 the subject is taking that may affect the subject's movement or condition and thus the measurements of the system, and a list of tests 325 that the subject has performed or perhaps are in queue for the subject to perform.

FIG. 3B depicts one screen of an embodiment of the graphical user interface (GUI) through which a user (e.g., subject or clinician) interacts with the system and the data. The screen depicted in the present embodiment shows a set input windows 330 and 355 whereby the user can input data regarding the subject, activities or tests, therapy or treatment, and the like which will be used to populate the results of the monitoring. The screen further depicts a pain response map 335 which graphically depicts in a two-dimensional representation the results (i.e., quantified pain measure) 350 based on various inputs or variables (axes of the graph) 340 and 345. The user can see the results 350 of the system's measurement and can interact with the data to change views, transmit the data, alter treatment or therapy protocols, or the like.

FIG. 4 depicts an alternative view from the pain response map in FIG. 3B in which actual sensor measurements are presented in graphical form as measured over time. In the particular embodiment depicted, individual signals from each of the x axis 400, y-axis 405 and z-axis 410 of gyroscope measurements are shown. This represents merely one example of an alternative view the user can select for display depending on the particular sensors and measurements used for the given embodiment. For example, other embodiments may display substantially real time physiological sensor recordings such as EEG, EKG, or the like waveforms, accelerometer data, or any combination of sensor measurements the system obtains.

FIG. 5 presents a number of outcome measures that can be measured or derived by the system in order to analyze the subject's physiological status. The measures 505 can be broken down into several domains 500 in order to more accurately classify and explain what each measure 505 describes or correlates with physiologically. Certain measures 515 relate to physical activity 510, and may include: percentage of the day spent moving, relationship between activity and rest periods, percentage of day in different body postures, and the like. Other measures 525 relate to mobility and community participation 520 of the subject, including: leg swing velocity, stride variability, double limb support time, number and duration of trips and stops, percentage of time spent at and away from home, and the like. Measures such as number and duration of trips and stops and percentage of time spent at or away from home are measured by or extracted from GPS data rather than motion sensors or other sensors related to physiological characteristics affected by pain. Other measures 535 relate to sleep quality 530, including: amount of time spent asleep, number of times awoken, sleep efficiency, and the like. Speech domain 540 measures 545 may also be used, such as alternating motion rate.

Figure 6:
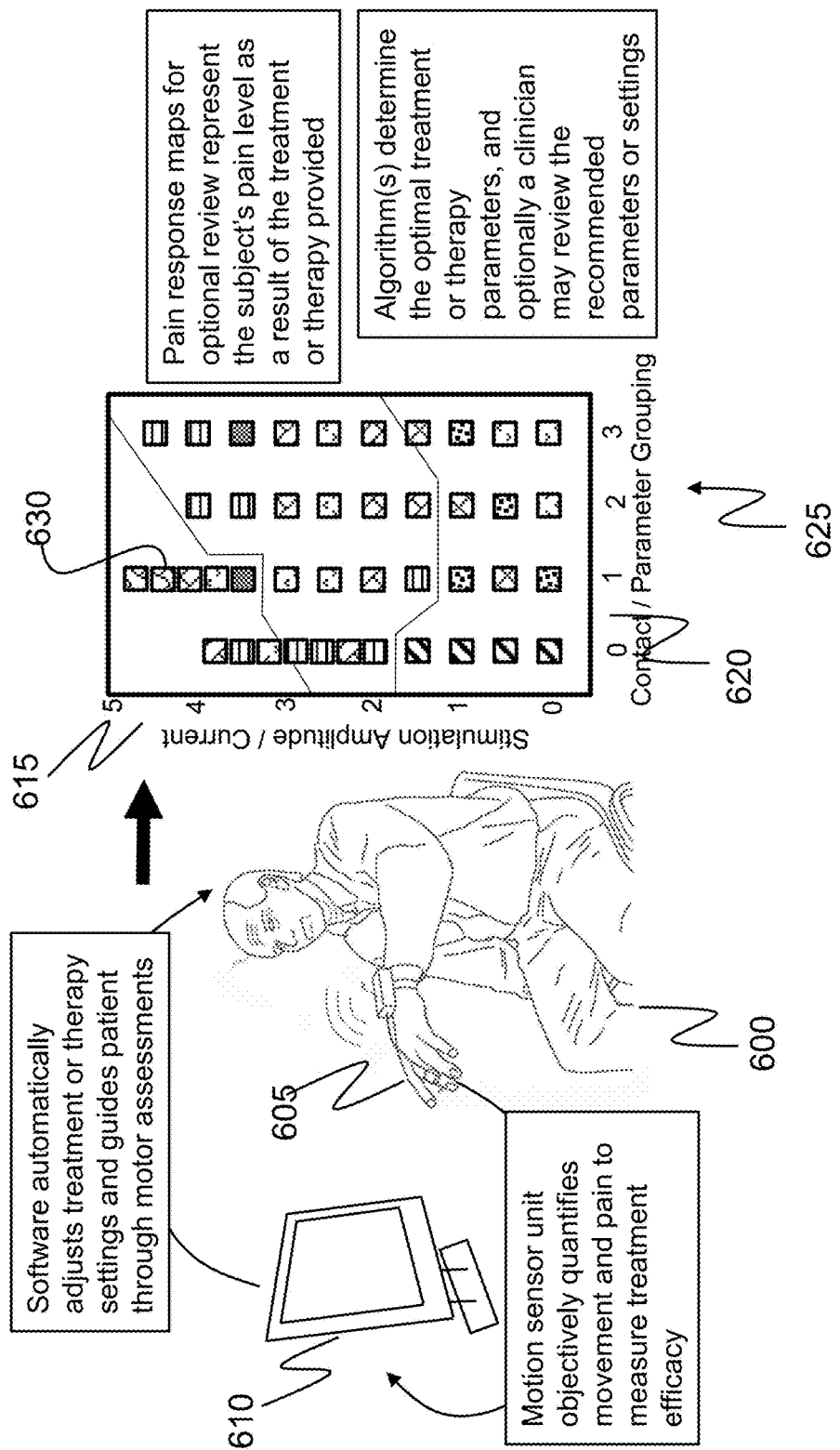
FIG. 6. Illustration of the monitoring process utilizing structured or instructed movement tasks for providing recommended treatment or therapy parameters or settings.

FIG. 6 depicts a method of the present invention utilizing an automated treatment or therapy system during guided testing. As the subject 600 performs tests, as instructed via a display 610 (automated), while wearing the subject-worn monitoring device 605, the system records and analyzes the results of those tests in light of the many variables. The system then populates a pain response map 625, in the background, to show the subject's response to the tested treatment or therapy parameters for each symptom while substantially simultaneously entering the same data into an algorithm(s) for quantifying the subject's level of pain and optionally for recommending new treatment or therapy parameters or settings. The axes 615 and 620 of the pain response map 625 may represent a single test variable, or may represent a grouping of variables or therapy settings or parameters that are used while the subject 600 conducts a test(s). The pain response map 625 is populated by visual results 630 representing the severity of the subject's 600 symptoms or pain level, or some other metric being measured, and the same data is entered into the algorithm(s). A clinician, technician or physician then determines, based on the test results, a set of treatment or therapy settings or parameters that are then entered into the subject's therapy device (not shown). Alternatively, the system may utilize the pain response map 625 to suggest treatment or therapy parameters or settings to the clinician, physician or technician for review. The parameters or settings are preferably optimized to meet a number of criteria or constraints, including best managing and addressing the subject's needs for comfort and pain alleviation, but also for maximizing performance of the system, for example through maximizing battery. The parameters are then entered into the subject's treatment or therapy device (not shown) for further testing or for delivering treatment and therapy to the subject.

Figure 7:
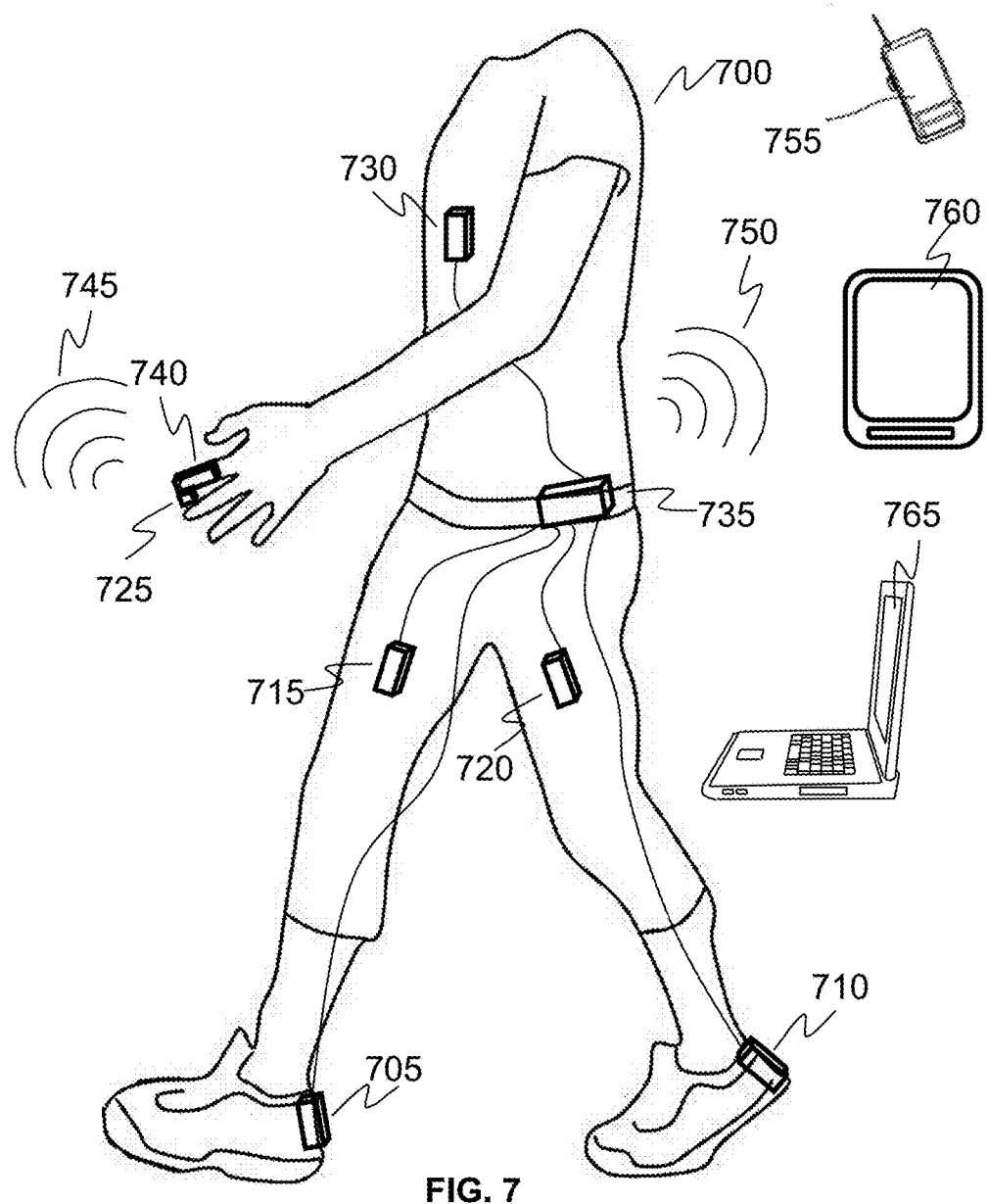
FIG. 7. Graphic depiction of a subject showing possible sensor and sensor unit placement options on multiple, separate parts of the subject's body either individually or simultaneously in multiple, separate locations for monitoring of the subject's movement and physiological status.

FIG. 7 illustrates possible sensor or sensor unit locations of a subject-worn monitoring or portable therapy system or device or system for different embodiments of the present invention for measuring or monitoring full body motion, or body motion from multiple, discrete body parts. The subject 700 in this particular embodiment is wearing six separate sensor units 705, 710, 715, 720, 725, 730 comprising accelerometers and gyroscopes (not shown) for recording movement data. The subject 700, in this embodiment, is depicted to be wearing at least one sensor unit on each foot 705, 710, thigh 715, 720, on one finger 725, and on the torso or trunk 730, though more sensors or sensor units may be placed in each, and/or other locations. Additionally, an optional, separate transceiver unit 735 for preprocessing and transmitting the movement data may be in wired (see connection to sensors/units on subject's heels, thighs and torso) or, more preferably, wireless communication 745 with wireless transmission components 740 one or more of the sensors (depicted only for the finger sensor 725, though optionally utilized for all sensors). The optional, separate transceiver unit 735 may further be in wired (not shown) or wireless 750 communication with the subject-worn monitoring device which may be a smartphone 755, tablet computer 760, laptop or other computer 765, or any other such device capable to be used as the portable therapy system or device. Alternatively, and preferably for some embodiments, no transceiver device may be present, and each of the sensors may be in direct communication with the processing device. The movement data from the optional, separate transceiver unit 735 or directly from the sensors is either stored for transfer at a later time or for immediate transmission to receiving circuitry or electronic components (not shown) on the portable therapy system or device via various mediums and any transmission protocols, for example, radio link, or by Bluetooth, WIFI, or even USB, or the like. The processor (not shown) of the portable therapy system or device 0755, 0760, or 0765 feeds the data into a trained algorithm preferably loaded into the processor. The trained algorithm then uses the measured movement data to determine, detect or predict symptoms of various disabilities or disorders and to quantify the amount of pain the subject is suffering, and outputs the determination in the form of a quantified pain index, pain response map data population, or parameters or settings for treatment or therapy either for clinician review or as input to control a treatment device such as an electric stimulator, automated medicine delivery or titration device, or the like.

Figure 8:
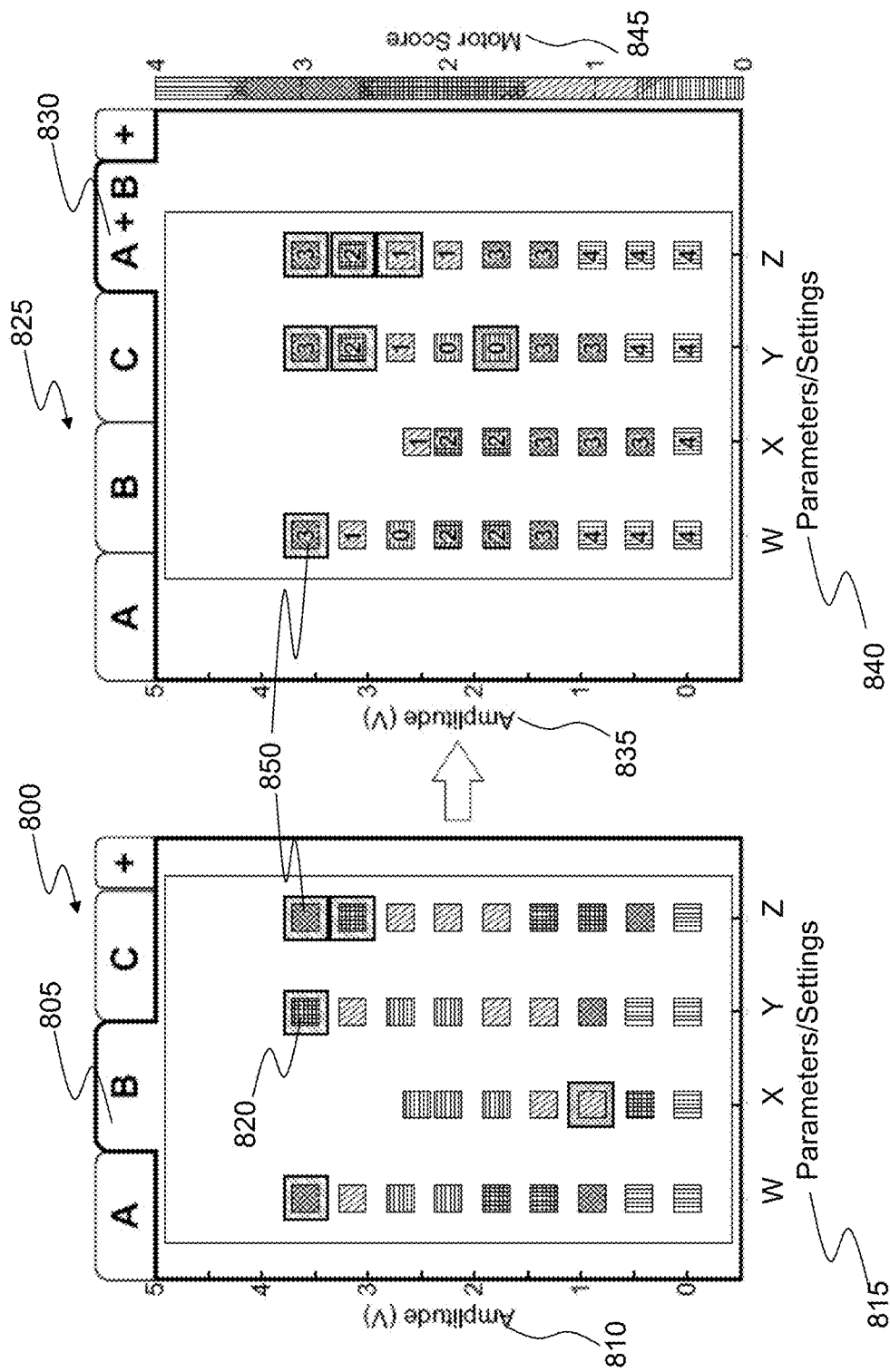
FIG. 8. Graphic depiction of one embodiment of pain response maps used to display test results and pain severity objectively measured by the system and displayed as a scatter plot of quantified pain severity scores.

FIG. 8 portrays one example of the pain response maps 800, 825 or other visual display tool or method for a particular embodiment with amplitude 810, 835 on the vertical axis and groupings of parameters or settings 815, 840 on the horizontal axis, in greater detail. Each task or test performed, activity or motion is represented by a separate tab 805 with its own pain response map 800, 825. Though the tabs 805 are labeled as A, B, C and A+B in the figure, in many preferred embodiments the tab 805 may be labeled with a number, the name of the task, test or activity it represents, an abbreviation thereof, or some other label indicating to the clinician, physician or technician what information is represented in the given tab 805. The amplitude 810, 835 is merely one example of a treatment or therapy parameter or setting (particularly for electrical stimulation devices) that can be used as a constant in monitoring the subject's pain response, and is used here as only an example, and is not intended to be limiting. In this example, amplitude is tracked along one vertical axis of the map 800, 825 for each grouping of parameters or settings 815, 840 that are used as shown on the horizontal axis, while the severity of the symptom detected or measured or quantified pain level 845 are shown on the other vertical axis 845 and correlated to an indicator 820 (e.g., cross-hatching pattern, color, or the like) of each individual test result box 850. Again, in many preferred embodiments, rather than the labeling the groupings of parameters or settings 815, 840 used to provide stimulation with letters (e.g., W, X, Y, Z in the figure), they may instead be labeled by a grouping number, grouping name, or any other labeling scheme or plan, which indicates to the clinician, physician, or technician which grouping of settings or parameters is represented. Preferably, the groupings are cross-referenced within the app, software and/or GUI such that a user, clinician, physician or technician may readily and easily be able to see what parameters or settings correspond to the chosen grouping label. The expanded example map view 825 portrays a new tab 830, which represents the combination of tabs A and B. This combination tab 830 represents the combination of the pain response maps for tasks or activities A and B, and the combination can be of any mathematical variety such as averaging, weighted averaging, or the like.

The combination task tab 830 is a result of the user selecting those two pain response maps to be combined together and optimized in some mathematical way (e.g., averaging) in order to show the results of how the pain response to each task or series of variables and inputs combine in order to optimize the treatment or therapy settings as well as other constraints. In other words, the goal is to minimize the level of treatment or therapy while simultaneously minimizing the subject's pain and/or the severity of the subject's symptoms and/or side effects. Combining the pain response maps for each task or activity or group of parameters and variables allows the user to see a combined result and select the treatment or therapy settings or parameters that are as close to optimal as possible. In a preferred embodiment, the system would be designed to be a closed-loop system, (i.e., for an implanted home-diagnostic and therapeutic device), which would not require extensive, or any, user input, but would perform the optimization automatically.

Figure 9:
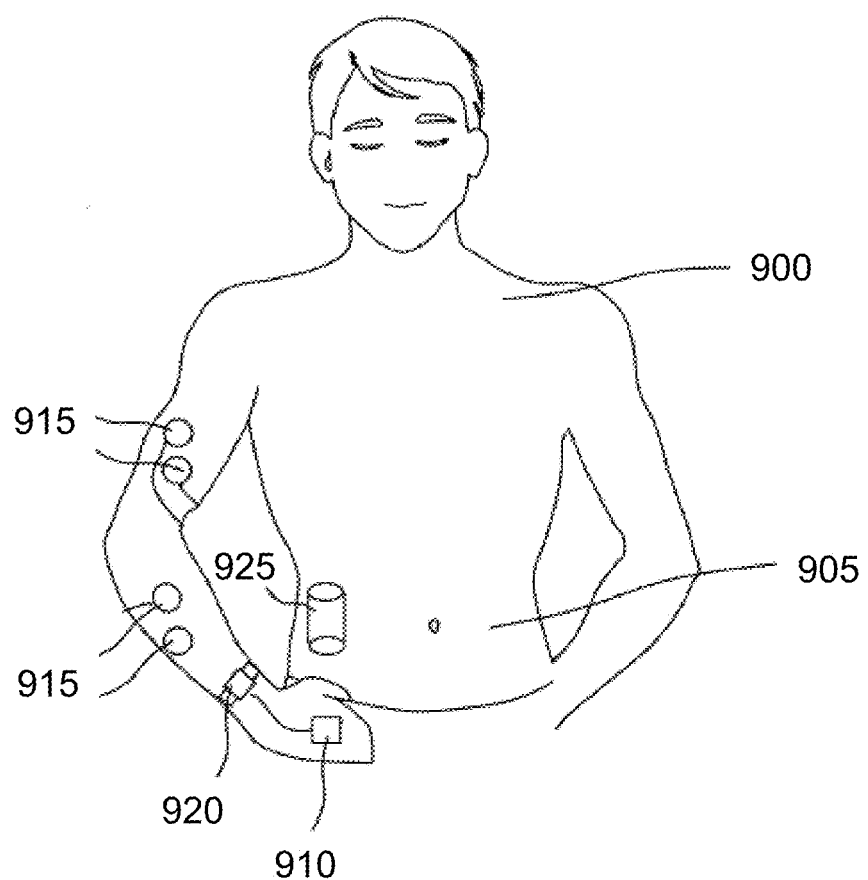
FIG. 9. Depiction of an optional treatment or therapy device that can be used in conjunction with the monitoring device of the present invention comprising an implanted treatment or therapy delivery system.

FIG. 9 is a diagram showing placement of various components of closed loop or semi-closed loop drug delivery system with drug or medication reservoir that can be used as a treatment or therapy device in conjunction with the monitoring device of the present invention. The system includes all of the components for measuring the subject's body movement, including, but not limited to, a sensors 915 and/or sensor modules 910, and a processing device 920 depicted as a smartwatch which may or may not be connected to or in communication with a smartphone (not shown), and adds a treatment or therapy device in the form of a drug delivery system 925, which includes a reservoir for holding medication or a drug with an embedded transceiver (not shown) and processor (not shown) and actuator (not shown) for allowing the drug delivery device to receive commands to dispense a certain amount of the drug, and a controller (not shown) for activating and deactivating the actuator based in part on the signal from the sensor(s) or processing device. In the depicted embodiment, a drug delivery device 925 is shown as implanted into the abdomen 905 of the subject 900. Alternatively, the drug deliver device 925 may be external and can be worn or attached to the subject by any device or methods known to those of skill in the art. The drug delivery device 925 contains a drug or medication, which is released into the subject's 900 body through activation of an actuator (not shown). This drug dispensing function is preferably initiated by the processing device 920 when it detects or makes a determination, via the embedded algorithms for processing the measured and calculated movement data, that the subject is experiencing pain or symptoms of a disability that warrants pharmaceutical intervention. All components can be in wired or wireless communication. Such embodiments can be fully closed-loop wherein control of the drug or medication delivery is controlled solely by the output of the processing device and its algorithms based on the measured and calculated or estimated measures or metrics, or can be semi-closed loop such that intervention, preferably by a clinician who may be located remotely, is either required or allowed in order to trigger the drug or medication delivery based on the output of the system and algorithm.

Figure 10:
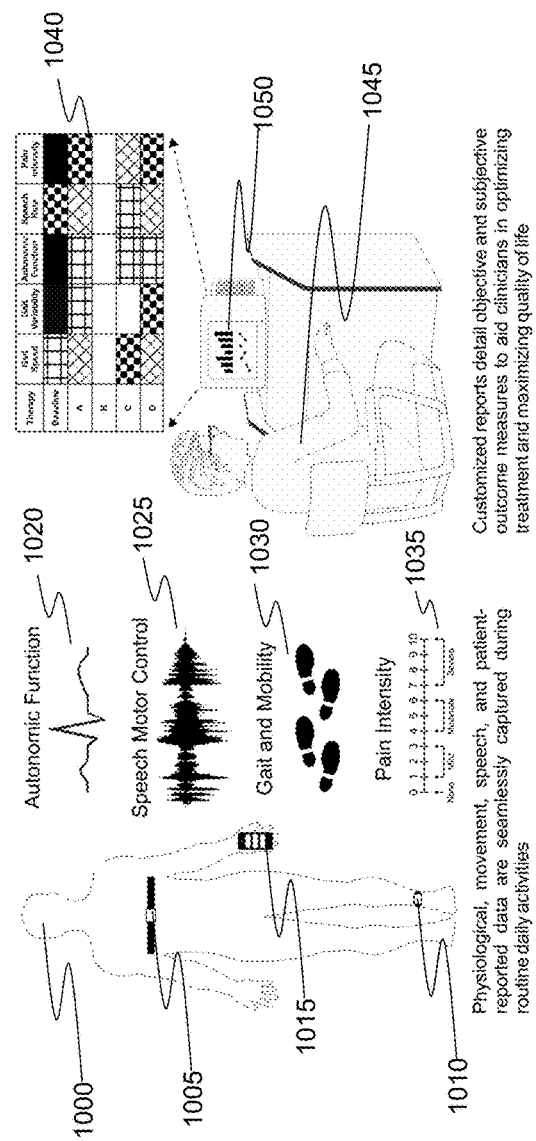
FIG. 10. Pictorial overview of operation of the system of the present invention whereby a subject's physiological status and movement are monitored and processed, and the system outputs a pain response report, where, optionally, a clinician reviews the reports for optimization of the treatment or therapy provided to the subject.

FIG. 10 presents a general overview of the function of the monitoring device of the present invention and the output of the system related to the subject's quantified level of pain based on the subject's measured and monitored movement. The subject 1000 dons the subject-worn monitoring device which comprises at least one (two are depicted, many more are possible) sensor or sensor unit 1005 and 1010. When the monitoring period begins or monitoring is otherwise initiated, the sensors 1005 and 1010 measure the subject's movement based on the particular sensor that is used (e.g., accelerometer, gyroscope, and/or the like) and transmit their measurements to a processing device 1015 which can be any processing device as described herein, but which is depicted as a smartphone. This system can record measurements and metrics from numerous domains for physiological and movement characteristics, including autonomous physiological signals 1020 (e.g., electromyogram (EMG), electrocardiogram (ECG), electroencephalogram (EEG), galvanic skin response, hear rate, and the like), speech motor control signals 1025, gait and mobility-related measurements 1030 as well as movement of other extremities or parts of the body, and pain intensity 1035 (e.g., patient self-reporting or recording). Many measures or metrics utilized by the system fit into at least one of these domains or categories, and the domains are merely intended to be exemplary of the various forms and groupings of data the system utilizes. Once the system processes the measured and calculated or estimated metrics or measures, it generates an output related to the amount of pain or disability the subject 1000 experienced or is experiencing during the monitoring period. The output can be in many forms including a numerical quantified pain index value, a visual representation of numerous iterations of variables and results, audio output, or any combination thereof. In the present figure, the output is depicted as a report 1040 that indicates value of several measures or metrics (gait speed, gait variability, autonomic function, speech rate, and pain intensity) during various tasks or activities (baseline and Task or Activity A through D). This report is output onto a display 1050 for review and analysis by a clinician, physician or technician 1045 who can then determine how much pain the subject is experiencing, what is most directly contributing to the pain, and what the best form of treatment or therapy is to address the subject's pain or disability.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A portable pain measurement and quantification device or system comprising:
   at least one sensor having a signal, the sensor adapted to measure a subject's external body movement or motion or a physiological signal associated with external body movement or motion and at least one sensor adapted to measure a subject's speech;
   a processor with an algorithm adapted to receive the signal from the at least one sensor and calculate a quantified pain level based at least in part on the measured external body movement or motion and at least in part on speech of the subject; and
   an output device adapted to output the quantified level of pain.

2. The portable device or system of claim 1, further comprising an input device adapted to allow the subject to input personal pain data corresponding to the subject's experiences, habits, activities or limitations encountered during a monitoring period.

3. The portable device or system of claim 1, further comprising a pain treatment or therapy device adapted to provide pain treatment or therapy to the subject based on the quantified pain level.

4. The portable device or system of claim 1, wherein the output device is a visual display adapted to the quantified pain level visually as a representation of the pain index value.

5. The portable device or system of claim 2, wherein the output device is a visual display adapted to the quantified pain level visually as a representation of the pain index value, and the output device further visually displays a subject-inputted subject pain index value.

6. The portable device or system of claim 5, wherein the processor and algorithm are further adapted to output a two-dimensional representation of a three-dimensional data display comprising quantified pain data based on various conditions, variables, constraints or inputs corresponding to the subject's measured external body movement or motion.

7. A portable pain measurement and quantification device or system comprising:
   at least one sensor having a signal, the sensor adapted to measure a subject's speech;
   a processor with an algorithm adapted to receive the signal from the at least one sensor and calculate a quantified pain level based at least in part on the measured speech; and
   an output device adapted to output the quantified level of pain.

8. The portable device or system of claim 7, further comprising an input device adapted to allow the subject to input personal pain data corresponding to the subject's experiences, habits, activities or limitations encountered during a monitoring period.

9. The portable device or system of claim 7, further comprising a pain treatment or therapy device adapted to provide pain treatment or therapy to the subject based on the quantified pain level.

10. The portable device or system of claim 7, further comprising at least one sensor adapted to measure a subject's external body motion or movement and the quantified pain level is calculated based on both the measured external body movement or motion and speech of the subject.

11. The portable device or system of claim 7, wherein the output device is a visual display adapted to the quantified pain level visually as a representation of the pain index value.

12. The portable device or system of claim 8, wherein the output device is a visual display adapted to the quantified pain level visually as a representation of the pain index value, and the output device further visually displays a subject-inputted subject pain index value.

13. A method of quantifying a level of a subject's pain comprising steps of:
   providing a portable pain measurement and quantification device to a subject, the pain measurement and quantification device comprising at least two sensors, each sensor having a signal, at least one sensor adapted to measure the subject's external body movement or motion or a physiological signal associated with external body movement or motion, and at least one sensor adapted to measure the subject's speech, an input device, a processor, and an output device;

measuring with the at least two sensors a first external body movement or motion of the subject and the subject's speech;

having the subject input, via the input device, personal pain data corresponding to the subject's experiences, habits, activities or limitations encountered while the pain measurement and quantification device was measuring the subject's external body movement or motion and speech;

calculating with a processor a quantified pain level of the subject based at least in part on the measured external body movement or motion and speech and at least in part on the personal pain data; and outputting via the output device at least quantified pain level.

14. The method of claim 13, further comprising the step of calculating the quantified pain level as a whole number pain index value on a scale of 0-10.

15. The method of claim 14, further comprising the step of displaying on the output device the quantified pain level visually as a representation of the pain index value.

16. The method of claim 13, further comprising the step of outputting a two-dimensional representation of a three-dimensional data display comprising quantified pain data based on various conditions, variables, constraints or inputs correlating to the subject's measured external body movement or motion, speech, and inputted personal pain data.

17. The method of claim 16, further comprising the step of measuring or calculating at least three physiological measures from the signals of the sensors, the at least three physiological measures being from the group consisting of percentage of the day spent moving, relationship between activity and rest periods, percentage of day in different body postures, leg swing velocity, stride variability, double limb support time, number and duration of trips and stops, percentage of time spent at and away from home, number and duration of trips and stops, percentage of time spent at or away from home, sleep quality, amount of time spent asleep, number of times awoken, and sleep efficiency.

18. The method of claim 17, wherein the quantified pain level is based on the measured external body movement or motion, the subject's speech and the at least three physiological measures, and the outputted two-dimensional pain data representation displays the quantified pain level as a whole number pain index value, on a scale of 0-10, based on groupings of conditions, variables and constraints, the groupings comprising combinations of the measured external body movement or motion, speech and at least three physiological measures.

19. The method of claim 13, further comprising the steps of providing a pain treatment or therapy device to the subject, the pain treatment or therapy device adapted to provide pain treatment or therapy to the subject based on the quantified pain level.

20. The device or system of claim 12, wherein the processor and algorithm are further adapted to output a two-dimensional representation of a three-dimensional data display comprising quantified pain data based on various conditions, variables, constraints or inputs corresponding to the subject's measured external body movement or motion.

* * * * *